US012357683B2

(12) United States Patent
Muthumani et al.

(10) Patent No.: US 12,357,683 B2
(45) Date of Patent: Jul. 15, 2025

(54) VACCINES AGAINST NIPAH VIRUS, AND METHODS OF USING SAME

(71) Applicant: THE WISTAR INSTITUTE OF ANATOMY AND BIOLOGY, Philadelphia, PA (US)

(72) Inventors: Kar Muthumani, Cherry Hill, NJ (US); David Weiner, Merion, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 786 days.

(21) Appl. No.: 17/269,409

(22) PCT Filed: Aug. 21, 2019

(86) PCT No.: PCT/US2019/047410
§ 371 (c)(1),
(2) Date: Feb. 18, 2021

(87) PCT Pub. No.: WO2020/041410
PCT Pub. Date: Feb. 27, 2020

(65) Prior Publication Data
US 2021/0252134 A1   Aug. 19, 2021

Related U.S. Application Data

(60) Provisional application No. 62/720,393, filed on Aug. 21, 2018.

(51) Int. Cl.
*A61K 39/155*  (2006.01)
*A61K 39/00*   (2006.01)
*A61P 31/14*   (2006.01)
*A61P 37/04*   (2006.01)
*C07K 14/005*  (2006.01)
*C12N 7/00*    (2006.01)

(52) U.S. Cl.
CPC ............ *A61K 39/155* (2013.01); *A61P 31/14* (2018.01); *A61P 37/04* (2018.01); *C07K 14/005* (2013.01); *C12N 7/00* (2013.01); *A61K 2039/53* (2013.01); *C12N 2760/18222* (2013.01); *C12N 2760/18234* (2013.01); *C12N 2760/18271* (2013.01)

(58) Field of Classification Search
CPC .. A61K 39/155; A61K 2039/53; A61K 39/12; A61P 31/14; A61P 37/04; A61P 31/12; C07K 14/005; C12N 7/00; C12N 2760/18222; C12N 2760/18234; C12N 2760/18271
See application file for complete search history.

(56) References Cited

U.S. PATENT DOCUMENTS

| | | | |
|---|---|---|---|
| 11,890,339 B2* | 2/2024 | Graham | A61K 39/12 |
| 2006/0053501 A1* | 3/2006 | George Courbot | A61P 31/12 435/5 |
| 2006/0134610 A1* | 6/2006 | Palese | C12Q 1/701 435/235.1 |
| 2007/0150972 A1 | 6/2007 | George Courbot | |
| 2010/0278862 A1 | 11/2010 | Audonnet | |
| 2011/0097355 A1 | 4/2011 | Morrison | |
| 2012/0301479 A1 | 11/2012 | Audonnet | |
| 2015/0050242 A1 | 2/2015 | Lee | |
| 2020/0030432 A1* | 1/2020 | Ciaramella | A61P 31/16 |
| 2021/0299242 A1* | 9/2021 | Graham | C07K 14/005 |

FOREIGN PATENT DOCUMENTS

| | | |
|---|---|---|
| CN | 1882704 | 12/2006 |
| CN | 101208104 | 6/2008 |

OTHER PUBLICATIONS

Choi H, Kudchodkar SB, Xu Z, Ho M, Xiao P, Ramos S, Humeau L, Weiner DB, Muthumani K. Elicitation of immune responses against Nipah virus by an engineered synthetic DNA vaccine. Front Virol. vol. 2, Nov. 10, 2022. (Year: 2022).*
Vijayachari P, Vedhagiri K, Mallilankaraman K, Mathur PP, Sardesai NY, Weiner DB, Ugen KE, Muthumani K. Immunogenicity of a novel enhanced consensus DNA vaccine encoding the leptospiral protein LipL45. Hum Vaccin Immunother. 2015; 11(8):1945-53. (Year: 2015).*
International Search Report and Written Opinion issued in App. No. PCT/US2019/047410, mailing date Nov. 22, 2019, 10 pages.

* cited by examiner

*Primary Examiner* — Rachel B Gill
(74) *Attorney, Agent, or Firm* — Riverside Law LLP

(57) ABSTRACT

An aspect of the present invention is related to nucleic acid constructs capable of expressing at least one Nipah virus (NiV) antigen that elicits an immune response in a mammal against NiV virus, and methods of use thereof.

13 Claims, 9 Drawing Sheets

Specification includes a Sequence Listing.

VACCINES AGAINST NIPAH VIRUS, AND METHODS OF USING SAME

CROSS-REFERENCE TO RELATED APPLICATIONS

This application is a U.S. national phase application filed under 35 U.S.C. § 371 claiming benefit to International Patent Application PCT/US19/47410, filed Aug. 21, 2019, which claims priority to U.S. provisional application No. 62/720,393, filed Aug. 21, 2018, the contents of each of which are incorporated herein in their entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: 206193-0007-00US_SequenceListing.txt created on Feb. 18, 2021, 31,271 bytes, is hereby incorporated by reference.

FIELD OF THE INVENTION

The present invention relates to a recombinant nucleotide sequence that encodes a Nipah viral antigen, and functional fragments thereof. The invention also relates to a combination of multiple recombinant nucleotide sequences encoding Nipah viral antigens for generating immunity against Nipah virus disease. The compositions of the invention provide improved methods for inducing immune responses, and for prophylactically and/or therapeutically immunizing individuals against Nipah virus.

BACKGROUND OF THE INVENTION

Nipah virus (NiV) is a member of the Paramyxoviridae family, first reported in 1998. On this occasion, pigs were the intermediate hosts. However, in subsequent NiV outbreaks, there were no intermediate hosts. In Bangladesh in 2004, humans became infected with NiV as a result of consuming date palm sap that had been contaminated by infected fruit bats. Human-to-human transmission has also been documented, including in a hospital setting in India.

NiV infection in humans has a range of clinical presentations. 5-14 days after transmission, an infected individual will exhibit symptoms such as flu like symptoms, fever and headache followed by drowsiness, disorientation, and mental confusion that can progress to coma within 24-48 hours. Patients with NiV infection typically exhibit severe pulmonary disease and encephalitis after an incubation period of 5-14 days, however NiV infection can stay latent and reactivate at a later date. This virus can cause long-term sequelae in those who survive acute infection.

Therefore, there remains a need to develop a vaccine for prophylaxis against NiV. The present invention addresses this need.

SUMMARY OF THE INVENTION

The invention provides an immunogenic composition comprising a nucleic acid molecule encoding at least one consensus Nipah virus (NiV) antigen.

In one embodiment, the NiV antigen is selected from the group consisting of a fusion antigen, a glycoprotein antigen, and a combination thereof.

In one embodiment, the nucleic acid molecule encodes a peptide comprising an amino acid sequence selected from the group consisting of: a) an amino acid sequence having at least about 90% identity over an entire length of the amino acid sequence selected from the group consisting of SEQ ID NO:2 and SEQ ID NO:6, b) an immunogenic fragment comprising at least about 90% identity over at least 60% of the amino acid sequence selected from the group consisting of SEQ ID NO:2 and SEQ ID NO:6, c) the amino acid sequence selected from the group consisting of SEQ ID NO:2 and SEQ ID NO:6, and d) an immunogenic fragment comprising at least 60% of the amino acid sequence selected from the group consisting of SEQ ID NO:2 and SEQ ID NO:6.

In one embodiment, the nucleic acid molecule is selected from the group consisting of a DNA molecule and a RNA molecule.

In one embodiment, the nucleic acid molecule comprises a nucleotide sequence selected from the group consisting of: a) a nucleotide sequence having at least about 90% identity over an entire length of a nucleotide sequence selected from the group consisting of SEQ ID NO:1 and SEQ ID NO:5, b) an immunogenic fragment of a nucleotide sequence having at least about 90% identity over at least 60% of the nucleotide sequence selected from the group consisting of SEQ ID NO:1 and SEQ ID NO:5, c) a nucleotide sequence selected from the group consisting of SEQ ID NO:1 and SEQ ID NO:5, and d) an immunogenic fragment of a nucleotide sequence selected from the group consisting of SEQ ID NO:1 and SEQ ID NO:5.

In one embodiment, the nucleotide sequence encoding the peptide is operably linked to at least one regulatory sequence selected from the group consisting of a start codon, an IgE leader sequence and a stop codon.

In one embodiment, the nucleic acid molecule encodes a peptide comprising an amino acid sequence selected from the group consisting of: a) an amino acid sequence having at least about 90% identity over an entire length of the amino acid sequence selected from the group consisting of SEQ ID NO:2 and SEQ ID NO:6, b) an immunogenic fragment comprising at least about 90% identity over at least 60% of the amino acid sequence selected from the group consisting of SEQ ID NO:2 and SEQ ID NO:6, c) the amino acid sequence selected from the group consisting of SEQ ID NO:2 and SEQ ID NO:6, and d) an immunogenic fragment comprising at least 60% of the amino acid sequence selected from the group consisting of SEQ ID NO:2 and SEQ ID NO:6; operably linked to an amino acid sequence as set forth in SEQ ID NO:9.

In one embodiment, the nucleic acid molecule comprises a nucleotide sequence selected from the group consisting of: a) a nucleotide sequence having at least about 90% identity over an entire length of a nucleotide sequence selected from the group consisting of SEQ ID NO:1 and SEQ ID NO:5, b) an immunogenic fragment of a nucleotide sequence having at least about 90% identity over at least 60% of the nucleotide sequence selected from the group consisting of SEQ ID NO:1 and SEQ ID NO:5, c) a nucleotide sequence selected from the group consisting of SEQ ID NO:1 and SEQ ID NO:5, and d) an immunogenic fragment of a nucleotide sequence selected from the group consisting of SEQ ID NO:1 and SEQ ID NO:5; operably linked to an nucleotide sequence encoding SEQ ID NO:9.

In one embodiment, the nucleic acid molecule comprises an expression vector.

In one embodiment, the nucleic acid molecule is incorporated into a viral particle.

In one embodiment, the immunogenic composition further comprises a pharmaceutically acceptable excipient.

In one embodiment, the immunogenic composition further comprises an adjuvant.

The invention also provides a method of inducing an immune response against a NiV antigen in a subject in need thereof. In one embodiment, the method comprises administering a composition comprising a nucleic acid molecule encoding at least one consensus Nipah virus (NiV) antigen to the subject.

In one embodiment, administering includes at least one of electroporation and injection.

The invention also provides a method of treating or preventing a NiV associated pathology in subject in need thereof. In one embodiment, the method comprises administering a composition comprising a nucleic acid molecule encoding at least one consensus Nipah virus (NiV) antigen to the subject.

In one embodiment, the NiV associated pathology is at least one of NiV infection and encephalitis.

BRIEF DESCRIPTION OF THE DRAWINGS

FIG. 1, comprising FIG. 1A depicts diagrams of expression constructs developed to express NiV-F immunogens. FIG. 1B depicts a diagram demonstrating that consensus NiV-F immunogens were designed from an analysis of multiple strains of NiV. FIG. 1C depicts exemplary data demonstrating expression of the consensus NiV antigens.

FIG. 2, comprising FIG. 2A depicts diagrams of a single expression construct developed to express NiV-G immunogens. FIG. 2B depicts a diagram demonstrating that consensus NiV-G immunogens were designed from an analysis of multiple strains of NiV. FIG. 2C depicts exemplary data demonstrating expression of the consensus NiV antigens.

FIG. 3, comprising

FIG. 4, comprising FIG. 4A depicts exemplary data demonstrating expression of the NiV-F recombinant envelope protein. FIG. 4B depicts exemplary data demonstrating expression of the NiV-G recombinant envelope protein.

FIG. 5, comprising FIG. 5A depicts serum titers of individual mice vaccinated with NiV-F using a 1× 25 µg vaccination schedule.

FIG. 5B depicts exemplary data demonstrating the presence of F-specific serum antibodies following vaccination.

FIG. 6, comprising FIG. 6A is a set of exemplary images demonstrating that the IgG antibody response induced by NiV-G was reactive analyzed by immunofluorescence analysis. FIG. 6B is an image depicting that NiV-G vaccine delivered in mice exhibited immune reactivity with recombinant NiV-G protein as compared to pVax1 alone.

FIG. 7, comprising

FIGS. 7C and 7D illustrate characterization of Nipah-specific dominant epitopes in C57BL/6 mice. IFN-g responses were assessed by ELISpot assays with matrix pools of peptides, indicating the presence of immunodominant epitopes composition of the Nipah-specific Fusion (7C) and Glycoprotein (7D). Values represent mean responses in each group (n=4)±SEM.

FIG. 7E shows flow cytometric analysis of T-cell responses induced by Nipah F vaccine. Immunization with Nipah-F induces higher number of IFN-g, TNF-α and IL-2 secreting cells when stimulated by Nipah-F peptides. One week after the last immunization with the Nipah-F vaccine, splenocytes were cultured in the presence of pooled Nipah-Fusion peptides or R10 only. Frequencies of Nipah-Fusion-specific IFN-g, NF-a and IL-2 secreting cells were measured by flow cytometry. Single function gates were set based on negative control (unstimulated) samples and were placed consistently across samples. The percentage of the total $CD8^+$ T-cell responses are shown. These data are representative of two independent immunization experiments. IFN, interferon; TNF, tumor necrosis factor.

DETAILED DESCRIPTION

Figures 1A, 1B, 1C:
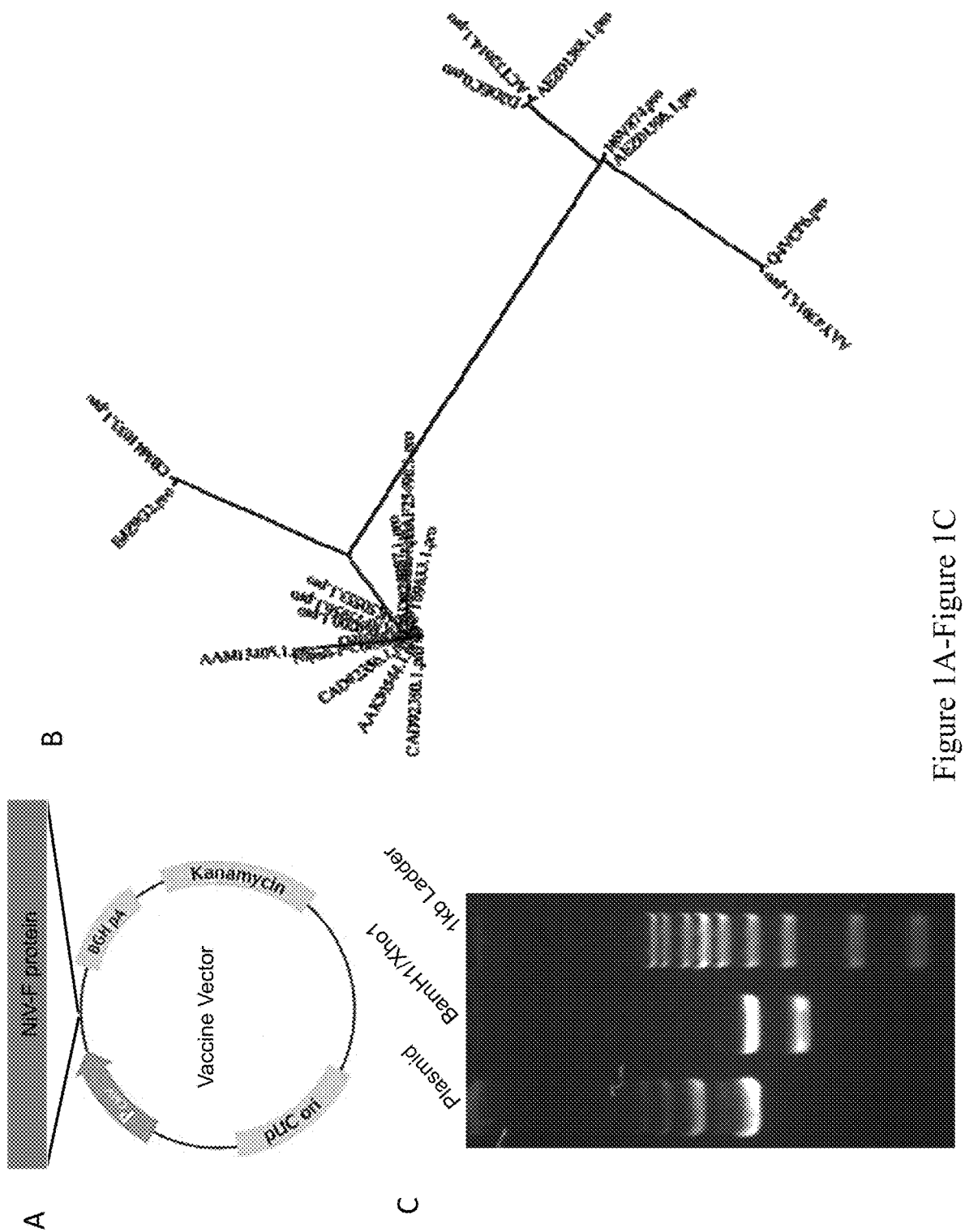
FIG. 1A through FIG. 1C, depicts the design for constructs expressing NiV-fusion(F) immunogens.

The present invention relates to a composition comprising a recombinant nucleic acid sequence that encodes one or more Nipah virus (NiV) antigens, and functional fragments thereof. The composition can be administered to a subject in need thereof to elicit an immune response in the subject against NiV virus.

In one embodiment, the composition comprises one or more nucleotide sequences capable of expressing one or more consensus NiV antigens in the subject and a pharmaceutically acceptable excipient. In one embodiment, the nucleic acid molecule comprises a promoter operably linked to a coding sequence that encodes one or more consensus NiV antigens. In one embodiment, one or more consensus NiV antigens are one or more of fusion and glycoprotein antigens. In one embodiment, the invention relates to a single nucleic acid construct for expression of both the fusion and glycoprotein consensus NiV antigens.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein may mean any molecule added to a nucleic acid vaccines to enhance antigenicity of the vaccine.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes an antigen as set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Consensus" or "consensus sequence" as used herein may mean a synthetic nucleotide sequence, or corresponding polypeptide sequence, constructed based on analysis of an alignment of multiple sequences (e.g., multiple sequences of a particular virus antigen.)

The term "constant current" is used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is effective for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a percentage of a full length polypeptide sequence or nucleotide sequence. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the full length of the parental nucleotide sequence or amino acid sequence or variant thereof.

"Genetic construct" as used herein refers to the DNA or RNA molecules that comprise a nucleotide sequence which encodes a protein, such as an antigen. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof Δ single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

The term "subtype" or "serotype" is used herein interchangeably and, in reference to a virus, means genetic variants of that virus antigen such that one subtype is recognized by an immune system apart from a different subtype.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of 2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within +2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

DESCRIPTION

The invention is based, in part on the development of an optimized consensus sequence encoding one or more Nipah virus (NiV) antigen. In one embodiment, the one or more NiV antigen encoded by the optimized consensus sequence is capable of eliciting an immune response in a mammal. In one embodiment, the NiV antigen encoded by the optimized consensus sequence can comprise an epitope(s) that makes it particularly effective as an immunogen against which an immune response can be induced.

The optimized consensus sequence can be a consensus sequence derived from two or more NiV antigens. The optimized consensus sequence can comprise a consensus sequence and/or modification(s) for improved expression. Modification can include codon optimization, RNA optimization, addition of a kozak sequence for increased translation initiation, and/or the addition of an immunoglobulin leader sequence to increase immunogenicity. The NiV antigen encoded by the optimized consensus sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The antigen encoded by the optimized consensus sequence can be designed to elicit stronger cellular and/or humoral immune responses than a corresponding non-optimized antigen.

Provided herein are NiV antigens that can be used to induce immunity against NiV in subjects with or at risk of NiV infection. In one embodiment, the present invention provides an immunogenic composition comprising one or more nucleic acid molecules that are capable of generating in a mammal an immune response against a NiV antigen. The present invention also provides isolated nucleic acid molecules that are capable of generating in a mammal an immune response against a NiV antigen. In one embodiment, the nucleic acid molecule comprises an optimized nucleotide sequence encoding a consensus NiV antigen.

Optimized Consensus NiV Antigens

In one embodiment, the present invention provides an immunogenic composition comprising one or more nucleic acid molecules that are capable of generating in a mammal an immune response against a NiV antigen. The present invention also provides isolated nucleic acid molecules that are capable of generating in a mammal an immune response against a NiV antigen. In one embodiment, the nucleic acid molecule comprises an optimized nucleotide sequence encoding at least 1, 2, 3 or more than 3 consensus NiV antigen. In one embodiment, one or more consensus antigens are consensus NiV fusion or glycoprotein antigens.

Consensus amino acid sequences for a NiV antigens include SEQ ID NO:2, SEQ ID NO:4, SEQ ID NO:6, SEQ ID NO:8 and variants thereof and fragments of SEQ ID NO:2, SEQ ID NO:4, SEQ ID NO:6, SEQ ID NO:8 and variants thereof An exemplary amino acid sequence of a synthetic consensus NiV-F is provided as SEQ ID NO:2. An exemplary amino acid sequence of a synthetic consensus NiV-G antigen is provided as SEQ ID NO:6.

In one embodiment, the invention provides compositions comprising a nucleic acid molecule comprising a nucleotide sequence that encodes a synthetic consensus NiV antigen. In one embodiment, a nucleotide sequence which encodes a synthetic consensus NiV-F antigen is provided as SEQ ID NO:1, which encodes SEQ ID NO:2. In one embodiment, a nucleotide sequence which encodes a synthetic consensus NiV-G antigen is provided as SEQ ID NO:5, which encodes SEQ ID NO:6.

Compositions that comprise one or more nucleotide sequence that encode multiple consensus NiV antigens may be on a single plasmid. In one embodiment, a composition comprises a single plasmid that encodes consensus NiV-F and NiV-G antigens under a single promoter. In such an embodiment, the sequence that encodes the NiV-F antigen and the sequence that encodes the NiV-G antigen may be linked by a fusion peptide sequence, for example a furin cleavage sequence.

In one embodiment, an optimized consensus encoded NiV antigen is operably linked to one or more regulatory elements. In one embodiment, a regulatory element is a leader sequence. In one embodiment, the leader sequence is an IgE leader sequence. In one embodiment, the IgE leader sequence has an amino acid sequence as set forth in SEQ ID NO:9. Therefore in one embodiment, the invention relates to an amino acid sequence as set forth in SEQ ID NO:2 or SEQ ID NO:6 operably linked to an amino acid sequence as set forth in SEQ ID NO:9. In one embodiment, the invention relates to a nucleotide sequence encoding an amino acid sequence as set forth in SEQ ID NO:2 or SEQ ID NO:6 operably linked to an amino acid sequence as set forth in SEQ ID NO:9. An exemplary amino acid sequence of a synthetic consensus NiV-F antigen operably linked to an IgE leader sequence is set forth in SEQ ID NO:4. An exemplary amino acid sequence of a synthetic consensus NiV-G antigen operably linked to an IgE leader sequence is set forth in SEQ ID NO:8. In one embodiment, the invention provides compositions comprising a nucleic acid molecule comprising a nucleotide sequence that encodes SEQ ID NO:4 or SEQ ID NO:8, or a variant or fragment thereof. In one embodiment, the nucleic acid molecule comprises a nucleotide sequence as set forth in SEQ ID NO:3 or SEQ ID NO:7, or a variant or fragment thereof.

In one embodiment, a regulatory element is a start codon. Therefore, in one embodiment, the invention relates to a nucleotide sequence as set forth in SEQ ID NO:1 or SEQ ID NO:5, or a fragment or variant thereof, operably linked to a nucleotide sequence comprising a start codon at the 5' terminus. In one embodiment, the invention relates to an amino acid sequence as set forth in SEQ ID NO:2 or SEQ ID NO:6, or a fragment or variant thereof, operably linked to an amino acid encoded by a start codon (e.g., a Methionine) at the N-terminus.

In one embodiment, a regulatory element is at least one stop codon. Therefore, in one embodiment, the invention relates to a nucleotide sequence as set forth in SEQ ID NO:1 or SEQ ID NO:5, or a fragment or variant thereof, operably linked to a nucleotide sequence comprising at least one stop codon at the 3' terminus. In one embodiment, the nucleotide sequence is operably linked to two stop codons to increase the efficiency of translational termination.

In one embodiment, nucleic acid molecule can encode a peptide having the amino acid sequence set forth in SEQ ID NO:2, SEQ ID NO:4, SEQ ID NO:6 or SEQ ID NO:8. In one embodiment, the nucleic acid molecule comprises the nucleotide sequence set forth in SEQ ID NO:1, SEQ ID NO:3, SEQ ID NO:5 or SEQ ID NO:7. In some embodiments, the sequence can be the nucleotide sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleotide sequence set forth in SEQ ID NO:1, SEQ ID NO:3, SEQ ID NO:5 or SEQ ID NO:7. In other embodiments, sequence can be the nucleotide sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2, SEQ ID NO:4, SEQ ID NO:6, or SEQ ID NO:8.

In some embodiments, the nucleic acid molecule comprises an RNA sequence that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleotide sequence set forth in SEQ ID NO:1, SEQ ID NO:3, SEQ ID NO:5 or SEQ ID NO:7. In some embodiments, the nucleic acid molecule comprises an RNA sequence that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the amino acid sequence set forth in SEQ ID NO:2 or SEQ ID NO:4.

The consensus-NiV antigen can be a peptide having the amino acid sequence set forth in SEQ ID NO:2, SEQ ID NO:4, SEQ ID NO:6 or SEQ ID NO:8. In some embodiments, the antigen can have an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2, SEQ ID NO:4, SEQ ID NO:6 or SEQ ID NO: 8.

Immunogenic fragments of SEQ ID NO:2, SEQ ID NO:4, SEQ ID NO:6 or SEQ ID NO:8 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of the full length of SEQ ID NO:2, SEQ ID NO:4, SEQ ID NO:6 or SEQ ID NO:8. In some embodiments, immunogenic fragments include a leader sequence, such as for example an immunoglobulin leader, such as the IgE leader. In some embodiments, immunogenic fragments are free of a leader sequence.

Immunogenic fragments of proteins with amino acid sequences homologous to immunogenic fragments of SEQ ID NO:2, SEQ ID NO:4, SEQ ID NO:6 or SEQ ID NO:8, can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:2, SEQ ID NO:4, SEQ ID NO:6 or SEQ ID NO:8. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

Some embodiments relate to immunogenic fragments of SEQ ID NO:1, SEQ ID NO:3, SEQ ID NO:5 or SEQ ID NO:7 comprising at least 60%, at least 65%, at least 70%, at least 75%, at least 80%, at least 85%, at least 90%, at least 95%, at least 96%, at least 97%, at least 98% or at least 99% of the full length of SEQ ID NO:1, SEQ ID NO:3, SEQ ID NO:5 or SEQ ID NO:7. Immunogenic fragments can be at least 96%, at least 97% at least 98% or at least 99% homologous to fragments of SEQ ID NO:1, SEQ ID NO:3, SEQ ID NO:5 or SEQ ID NO:7. In some embodiments, immunogenic fragments include sequences that encode a leader sequence, such as for example an immunoglobulin leader, such as the IgE leader. In some embodiments, fragments are free of coding sequences that encode a leader sequence.

In one embodiment, the nucleic acid molecule comprises a sequence at least 90% homologous to SEQ ID NO:1, SEQ ID NO:3, SEQ ID NO:5 or SEQ ID NO:7.

In one embodiment, the nucleic acid molecule comprises an RNA sequence encoding a consensus NiV antigen sequence described herein. For example, nucleic acids may comprise an RNA sequence encoding one or more of SEQ ID NO:2, SEQ ID NO:4, SEQ ID NO:6 or SEQ ID NO:8, a variant thereof, a fragment thereof or any combination thereof.

Nucleic Acid Constructs

When taken up by a cell, the DNA plasmids can remain in the cell as separate genetic material. Alternatively, RNA may be administered to the cell. It is also contemplated to provide a genetic construct as a linear minichromosome including a centromere, telomeres and an origin of replication. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered. Such genetic constructs may be therefore be recombinant nucleic acid molecules.

The recombinant nucleic acid molecule can include one or more recombinant nucleotide sequence constructs. The recombinant nucleotide sequence construct can include one or more components, which are described in more detail below.

The recombinant nucleotide sequence construct can include a heterologous nucleotide sequence that encodes a viral antigen, a fragment thereof, a variant thereof, or a combination thereof. The recombinant nucleotide sequence construct can also include a heterologous nucleotide sequence that encodes a protease or peptidase cleavage site. The recombinant nucleotide sequence construct can also include a heterologous nucleotide sequence that encodes an internal ribosome entry site (IRES). An IRES may be either a viral IRES or an eukaryotic IRES. The recombinant nucleotide sequence can include one or more leader sequences, in which each leader sequence encodes a signal peptide. The recombinant nucleotide sequence can include one or more promoters, one or more introns, one or more transcription termination regions, one or more initiation codons, one or more termination or stop codons, and/or one or more polyadenylation signals. The recombinant nucleotide sequence construct can also include one or more linker or tag sequences. The tag sequence can encode a hemagglutinin (HA) tag.

a) Protease Cleavage Site

The recombinant nucleotide sequence construct can include heterologous nucleotide sequence encoding a protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a furin cleavage site.

b) Linker Sequence

The recombinant nucleotide sequence construct can include one or more linker sequences. The linker sequence can spatially separate or link the one or more components described herein. In other embodiments, the linker sequence can encode an amino acid sequence that spatially separates or links two or more polypeptides.

c) Promoter

The recombinant nucleotide sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleotide sequence construct as it is from the transcription start site in its natural setting. However, variation in this distance may be accommodated without loss of promoter function.

The promoter may be operably linked to the heterologous nucleotide sequence encoding one or more viral antigen. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metallothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

d) Transcription Termination Region

The recombinant nucleotide sequence construct can include one or more transcription termination regions. The transcription termination region can be downstream of the coding sequence to provide for efficient termination. The transcription termination region can be obtained from the same gene as the promoter described above or can be obtained from one or more different genes.

e) Initiation Codon

The recombinant nucleotide sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

f) Termination Codon

The recombinant nucleotide sequence construct can include one or more termination or stop codons. The termination codon can be downstream of the coding sequence. The termination codon can be in frame with the coding sequence. The termination codon can be associated with one or more signals required for efficient translation termination. Initiation codons and stop codon are generally considered to be part of a nucleotide sequence that encodes the desired protein. However, it is necessary that these elements are functional in the mammals to whom the nucleic acid construct is administered. The initiation and termination codons must be in frame with the coding sequence.

g) Polyadenylation Signal

The recombinant nucleotide sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human 3-globin polyadenylation signal. The SV40 polyadenylation signal may be a polyadenylation signal from a pCEP4 plasmid (Invitrogen, San Diego, CA). Promoters and polyadenylation signals used must be functional within the cells of the individual.

h) Leader Sequence

The recombinant nucleotide sequence construct can include one or more leader sequences. The leader sequence can encode a signal peptide. The signal peptide can be an immunoglobulin (Ig) signal peptide, for example, but not limited to, an IgG signal peptide and a IgE signal peptide.

In addition to regulatory elements required for DNA expression, as described above, other elements may also be included in the recombinant nucleic acid molecule. Such additional elements include enhancers. The enhancer may be selected from the group including but not limited to: human actin, human myosin, human hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, CA) contain the Epstein Barr virus origin of replication and nuclear antigen EBNA-1 coding region which produces high copy episomal replication without integration.

In order to maximize protein production, regulatory sequences may be selected which are well suited for gene expression in the cells the construct is administered into. Moreover, codons that encode said protein may be selected which are most efficiently transcribed in the host cell. One having ordinary skill in the art can produce DNA constructs that are functional in the cells.

In some embodiments, nucleic acid constructs may be provided in which the coding sequences for the proteins described herein are linked to IgE leader peptide, or such IgE leader is removed. In some embodiments, proteins described herein are linked to IgE signal peptide, or such IgE leader is removed.

In some embodiments for which protein is used, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well-known expression systems. For example, the commercially available plasmid pSE420 (Invitrogen, San Diego, Calif) may be used for production of protein in *Escherichia coli* (*E. coli*). The commercially available plasmid pYES2 (Invitrogen, San Diego, Calif) may, for example, be used for production in *Saccharomyces cerevisiae* strains of yeast. The commercially available MAXBAC™ complete baculovirus expression system (Invitrogen, San Diego, Calif) may, for example, be used for production in insect cells. The commercially available plasmid pcDNA or pcDNA3 (Invitrogen, San Diego, Calif.) may, for example, be used for production in mammalian cells such as Chinese hamster ovary (CHO) cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989)). Thus, the desired proteins can be prepared in both prokaryotic and eukaryotic systems, resulting in a spectrum of processed forms of the protein.

Vector

The recombinant nucleotide sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleotide sequence construct is produced by the cellular-transcription and translation machinery ribosomal complexes. The one or more vectors can express large amounts of stable messenger RNA, and therefore proteins.

i) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleotide sequence construct may be chimeric, meaning that at least one of its components is heterologous with respect to at least one of its other components.

j) Plasmid

The one or more vectors can be a plasmid. The plasmid may be useful for transfecting cells with the recombinant nucleotide sequence construct. The plasmid may be useful for introducing the recombinant nucleotide sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif), which may be used for protein production in *Escherichia coli* (*E. coli*). The plasmid may also be pYES2 (Invitrogen, San Diego, Calif), which may be used for protein production in *Saccharomyces cerevisiae* strains of yeast. The plasmid may also be of the MAXBAC™ complete baculovirus expression system (Invitrogen, San Diego, Calif), which may be used for protein production in insect cells. The plasmid may also be pcDNAI or pcDNA3 (Invitrogen, San Diego, Calif), which may be used for protein production in mammalian cells such as Chinese hamster ovary (CHO) cells.

k) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to SEQ ID NO:1, SEQ ID NO:3, SEQ ID NO:5 or SEQ ID NO:7. In another embodiment, the nucleotide sequence comprises an RNA sequence transcribed by a DNA sequence encoding a polypeptide sequence of SEQ ID NO:2, SEQ ID NO:4, SEQ ID NO:6 or SEQ ID NO:8, or a variant thereof or a fragment thereof. Accordingly, in one embodiment, the invention provides an RNA molecule encoding one or more consensus NiV antigen. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

l) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleotide sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleotide sequence construct. The LEC may be any linear DNA devoid of any phosphate backbone. The LEC may not contain any antibiotic resistance genes and/or a phosphate backbone. The LEC may not contain other nucleotide sequences unrelated to the desired gene expression.

The LEC may be derived from any plasmid capable of being linearized. The plasmid may be capable of expressing the heavy chain polypeptide and/or light chain polypeptide encoded by the recombinant nucleotide sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleotide sequence construct.

The LEC can be pcrM2. The LEC can be pcrNP. pcrNP and pcrMR can be derived from pNP (Puerto Rico/34) and pM2 (New Caledonia/99), respectively.

m) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

n) Method of Preparing the Vector

Provided herein is a method for preparing the one or more vectors in which the recombinant nucleotide sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

Vaccines and Immunogenic Compositions

Immunogenic compositions, such as vaccines, are provided comprising an optimized consensus sequence, an optimized consensus-encoded antigen, a fragment thereof, a variant thereof, or a combination thereof. The immunogenic composition can significantly induce an immune response of a subject administered with the immunogenic composition against the NiV antigen. The vaccine may comprise a plurality of the nucleic acid molecules, or combinations thereof. The vaccine may be provided to induce a therapeutic or prophylactic immune response.

The immunogenic composition can be a DNA vaccine, an RNA vaccine, a peptide vaccine, or a combination vaccine. The vaccine can include an optimized consensus nucleotide sequence encoding an antigen. The nucleotide sequence can be DNA, RNA, cDNA, a variant thereof, a fragment thereof, or a combination thereof. The nucleotide sequence can also include additional sequences that encode linker, leader, or tag sequences that are linked to the antigen by a peptide bond. The peptide vaccine can include an antigen, a variant thereof, a fragment thereof, or a combination thereof. The combination DNA and peptide vaccine can include the above described optimized consensus nucleotide sequence and the encoded antigen.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the one or more NiV antigens. The RNA vaccine can be introduced into the cell.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing protective T cell responses; and providing ease of administration, few side effects, biological stability, and low cost per dose.

Provided herein is an immunogenic composition capable of generating in a mammal an immune response against NiV. The immunogenic composition may comprise each plasmid as discussed above. The immunogenic composition may comprise a plurality of the plasmids, or combinations thereof. The immunogenic composition may be provided to induce a therapeutic or prophylactic immune response.

Immunogenic compositions may be used to deliver nucleic acid molecules that encode one or more consensus NiV antigen. Immunogenic compositions are preferably compositions comprising plasmids.

Another aspect of the present invention provides immunogenic compositions that are capable of generating in a mammal an immune response against one or more NiV viruses. The immunogenic compositions are comprised of one or more nucleic acid molecules capable of expressing a consensus viral antigens in the mammal.

In one embodiment, the immunogenic composition comprises a nucleotide sequence that encodes at least one consensus NiV antigen. The consensus viral antigens may be consensus fusion, consensus glycoprotein or a combination of one or more of aforementioned antigens.

Each antigen can be associated with viral infection. In one embodiment, each antigen can be associated with a NiV virus infection.

The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

In some embodiments, the immunogenic composition comprises a plurality of unique nucleic acid molecules, wherein each of the plurality of unique nucleic acid molecules encodes a consensus fusion protein or consensus glycoprotein protein.

Exemplary nucleic acid molecules that can be included in the immunogenic composition of the invention may be selected from:

| SEQ ID NO: | Type | Description |
| --- | --- | --- |
| 1 | Nucleotide | Consensus NiV Fusion (F) antigen |
| 2 | Amino Acid | Consensus NiV glycoprotein (G) antigen |
| 3 | Nucleotide | Consensus NiV fusion (F) antigen operably linked to an IgE leader sequence |
| 4 | Amino Acid | Consensus NiV fusion (F) antigen operably linked to an IgE leader sequence |
| 5 | Nucleotide | Consensus NiV glycoprotein (G) antigen |
| 6 | Amino Acid | Consensus NiV glycoprotein (G) antigen |
| 7 | Nucleotide | Consensus NiV glycoprotein (G) antigen operably linked to an IgE leader sequence |
| 8 | Amino Acid | Consensus NiV glycoprotein (G) antigen operably linked to an IgE leader sequence |

In one embodiment, the nucleic acid molecule comprises a optimized nucleic acid sequence. The optimized sequence can comprise a consensus sequence and/or modification(s) for improved expression. Modification can include codon optimization, RNA optimization, addition of a kozak sequence for increased translation initiation, and/or the addition of an immunoglobulin leader sequence to increase immunogenicity. The NiV antigen encoded by the optimized sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The NiV antigen encoded by the optimized sequence can be designed to elicit stronger cellular and/or humoral immune responses than a corresponding native antigen.

The immunogenic composition can induce an immune response in the subject administered the composition. The induced immune response can be specific for at least one NiV antigen. The induced immune response can be reactive with at least one NiV antigen related to an administered optimized consensus-encoded antigen. In various embodiments, related antigens include antigens having amino acid sequences having at least 90%, at least 91%, at least 92%, at least 93%, at least 94%, at least 95%, at least 96%, at least 97%, at least 98%, at least 99%, or 100% homology to the amino acid sequence of the optimized consensus-encoded antigen. In various embodiments, related antigens include antigens encoded by nucleotide sequences having at least 90%, at least 91%, at least 92%, at least 93%, at least 94%, at least 95%, at least 96%, at least 97%, at least 98%, at least 99%, or 100% homology to the optimized consensus nucleotide sequences disclosed herein.

The immunogenic composition can induce a humoral immune response in the subject administered the immunogenic composition. The induced humoral immune response can be specific for at least one NiV antigen. The induced humoral immune response can be reactive with at least one NiV antigen related to an administered optimized consensus-encoded antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition of the invention.

The humoral immune response induced by the immunogenic composition can include an increased level of IgG antibodies associated with the subject administered the immunogenic composition as compared to a subject not administered the immunogenic composition. These IgG antibodies can be specific for at least one NiV antigen genetically related to an administered optimized consensus-encoded antigen. These IgG antibodies can be reactive with at least one NiV antigen genetically related to an administered optimized consensus-encoded antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition.

The immunogenic composition can induce a cellular immune response in the subject administered the immunogenic composition. The induced cellular immune response can be specific for at least one NiV antigen genetically related to an administered optimized consensus-encoded antigen. The induced cellular immune response can be reactive at least one NiV antigen genetically related to an administered optimized consensus-encoded antigen. The induced cellular immune response can include eliciting a CD8+ T cell response. The elicited CD8+ T cell response can be reactive with at least one NiV antigen genetically related to an administered optimized consensus-encoded antigen. The elicited CD8+ T cell response can be polyfunctional. The induced cellular immune response can include eliciting a CD8+ T cell response, in which the CD8+ T cells produce interferon-gamma (IFN-γ), tumor necrosis factor alpha (TNF-α), interleukin-2 (IL-2), or a combination of IFN-γ and TNF-α.

The induced cellular immune response can include an increased CD8+ T cell response associated with the subject administered the immunogenic composition as compared to the subject not administered the immunogenic composition. The CD8+ T cell response associated with the subject administered the immunogenic composition can be increased by about 2-fold to about 30-fold, about 3-fold to about 25-fold, or about 4-fold to about 20-fold as compared to the subject not administered the immunogenic composition. The CD8+ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition.

The induced cellular immune response can include an increased frequency of CD107a/IFNγ/T-bet triple-positive CD8 T cells that are reactive against the native antigen. The frequency of CD107a/IFNγ/T-bet triple-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition.

The induced cellular immune response can include an increased frequency of CD107a/IFNγ double-positive CD8 T cells that are reactive against the native antigen. The frequency of CD107a/IFNγ double-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition.

The cellular immune response induced by the immunogenic composition can include eliciting a CD4+ T cell response. The elicited CD4+ T cell response can be reactive with the native antigen genetically related to the optimized consensus antigen. The elicited CD4+ T cell response can be polyfunctional. The induced cellular immune response can include eliciting a CD4+ T cell response, in which the CD4+ T cells produce IFN-γ, TNF-α, IL-2, or a combination of IFN-γ and TNF-α.

The induced cellular immune response can include an increased frequency of CD4+ T cells that produce IFN-γ. The frequency of CD4+IFN-γ+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition.

The induced cellular immune response can include an increased frequency of CD4+ T cells that produce TNF-α. The frequency of CD4+TNF-α+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic composition.

The induced cellular immune response can include an increased frequency of CD4+ T cells that produce both IFN-γ and TNF-α. The frequency of CD4+IFN-γ+TNF-α+ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition.

Other Components of the Composition

In some embodiments, the immunogenic composition of the invention further includes a pharmaceutically acceptable excipient. A pharmaceutically acceptable excipient can include such functional molecules as vehicles, adjuvants, carriers or diluents, which are known and readily available to the public. Preferably, the pharmaceutically acceptable excipient is an adjuvant or transfection facilitating agent. In some embodiments, the nucleic acid molecule, or DNA plasmid, is delivered to the cells in conjunction with administration of a polynucleotide function enhancer or a genetic vaccine facilitator agent (or transfection facilitating agent). Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in US. Serial Number 021, 579 filed Apr. 1, 1994, which is incorporated herein by reference. The transfection facilitating agent can be administered in conjunction with nucleic acid molecules as a mixture with the nucleic acid molecule or administered separately simultaneously, before or after administration of nucleic acid molecules. Examples of transfection facilitating agents includes surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

In some embodiments of the present invention, the immunogenic compositions can further include an adjuvant. In some embodiments, the adjuvant is selected from the group consisting of: alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. Other genes which may be useful adjuvants include those encoding: MCP-1, MIP-1-alpha, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. In some preferred embodiments, the adjuvant is selected from IL-12, IL-15, CTACK, TECK, or MEC.

The immunogenic compositions according to the present invention are formulated according to the mode of administration to be used. In cases where DNA plasmid vaccines are injectable compositions, they are sterile, and/or pyrogen free and/or particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. In some embodiments, a stabilizing agent that allows the formulation to be stable at room or ambient temperature for extended periods of time, such as LGS or other polycations or polyanions is added to the formulation.

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Serial No. 021,579 filed Apr. 1, 1994, which is fully incorporated by reference.

The composition may comprise nucleic acid at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of nucleic acid. In some preferred embodiments, composition can contain about 10 nanograms to about 800 micrograms of nucleic acid. In some preferred embodiments, the composition can contain about 0.1 to about 500 micrograms of nucleic acid. In some preferred embodiments, the composition can contain about 1 to about 350 micrograms of nucleic acid. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of nucleic acid.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

Methods of Delivery of the Composition

Another aspect of the present invention provides methods of eliciting an immune response against one or more NiV virus in a mammal, comprising delivering an immunogenic composition to tissue of the mammal, the immunogenic composition comprising at least one nucleic acid molecule capable of expressing a consensus antigen of the one or more NiV virus in a cell of the mammal to elicit an immune response in the mammal.

The present invention also relates to methods of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Applications Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

In one embodiment, the nucleic acid formulations for use with a muscle or skin EP device described herein have high nucleic acid concentrations, preferably concentrations that include microgram to tens of milligram quantities, and preferably milligram quantities, of nucleic acid in small volumes that are optimal for delivery to the skin, preferably small injection volume, ideally 25-200 microliters (µL). In some embodiments, the nucleic acid formulations have high nucleic acid concentrations, such as 1 mg/mL or greater (mg nucleic acid/volume of formulation). More preferably, the nucleic acid formulation has a nucleic acid concentration that provides for gram quantities of nucleic acid in 200 µL of formula, and more preferably gram quantities of nucleic acid in 100 µL of formula.

The nucleic acid plasmids for use with the EP devices of the present invention can be formulated or manufactured using a combination of known devices and techniques, but preferably they are manufactured using an optimized plasmid manufacturing technique that is described in U.S. application Ser. No. 12/126,611 which published as US Publication No. 20090004716, which published Jan. 1, 2009. In some examples, the nucleic acid plasmids used in these studies can be formulated at concentrations greater than or equal to 10 mg/mL. The manufacturing techniques also include or incorporate various devices and protocols that are commonly known to those of ordinary skill in the art, in addition to those described in US Publication No. 20090004716 and those described in U.S. Pat. No. 7,238,522, which issued on Jul. 3, 2007. The high concentrations of plasmids used with the skin EP devices and delivery techniques described herein allow for administration of plasmids into the ID/SC space in a reasonably low volume and aids in enhancing expression and immunization effects. The publications, US Publication No. 20090004716 and U.S. Pat. No. 7,238,522, are hereby incorporated in their entirety.

Method of Treatment

Also provided herein is a method of treating, protecting against, and/or preventing disease in a subject in need thereof by inducing an immune response against a viral antigen in the subject. In certain embodiments, the invention provides a method of treating, protecting against, and/or preventing at least one of a NiV virus infection or a NiV associated pathology in a subject. In one embodiment, a NiV associated pathology is encephalitis.

The method can include administering an immunogenic composition of the invention to the subject. Administration of the composition to the subject can be done using the method of delivery described above.

The composition dose can be between 1 µg to 10 mg active component/kg body weight/time, and can be 20 µg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

Combination Vaccine

The present invention also provides a method of treating, protecting against, and/or preventing disease in a subject in need thereof by administering a combination of two or more nucleic acid molecules or immunogenic compositions wherein each of the two or more nucleic acid molecules or immunogenic compositions encodes an optimized consensus viral antigen.

The two or more nucleic acid molecules or immunogenic compositions may be administered using any suitable method such that a combination of two or more nucleic acid molecules or immunogenic compositions are both present in the subject. In one embodiment, the method may comprise administration of a first nucleic acid molecule or immunogenic composition of the invention by any of the methods described in detail above and administration of a second nucleic acid molecule or immunogenic composition less than 1, less than 2, less than 3, less than 4, less than 5, less than 6, less than 7, less than 8, less than 9 or less than 10 days following administration of the first nucleic acid molecule or immunogenic composition of the invention. In one embodiment, the method may comprise administration of at least 2, at least 3, at least 4, at least 5, at least 6 or more than 6 nucleic acid molecules or immunogenic compositions concurrently at different sites on the same subject. In one embodiment, the method may comprise administration of at least 2, at least 3, at least 4, at least 5, at least 6 or more than 6 nucleic acid molecules or immunogenic compositions more than 1, more than 2, more than 3, more than 4, more than 5, more than 6, more than 7, more than 8, more than 9 or more than 10 days following administration of a first nucleic acid molecule or immunogenic composition. In one embodiment, the method may comprise administration of at least 2, at least 3, at least 4, at least 5, at least 6 or more than 6 nucleic acid molecules or immunogenic compositions less than 1, less than 2, less than 3, less than 4, less than 5, less than 6, less than 7, less than 8, less than 9 or less than 10 days following administration of a first nucleic acid molecule or immunogenic composition.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: Construction & Characterization of Immune Responses to Novel Synthetic DNA Vaccines Against Nipah Virus DNA vaccines have been developed to elicit the immune responses against consensus viral proteins of various emerging infectious diseases. The current invention demonstrates the development and use of a Nipah vaccine to induce an immune response in a vaccinated subject.

Figures 2A, 2B, 2C:
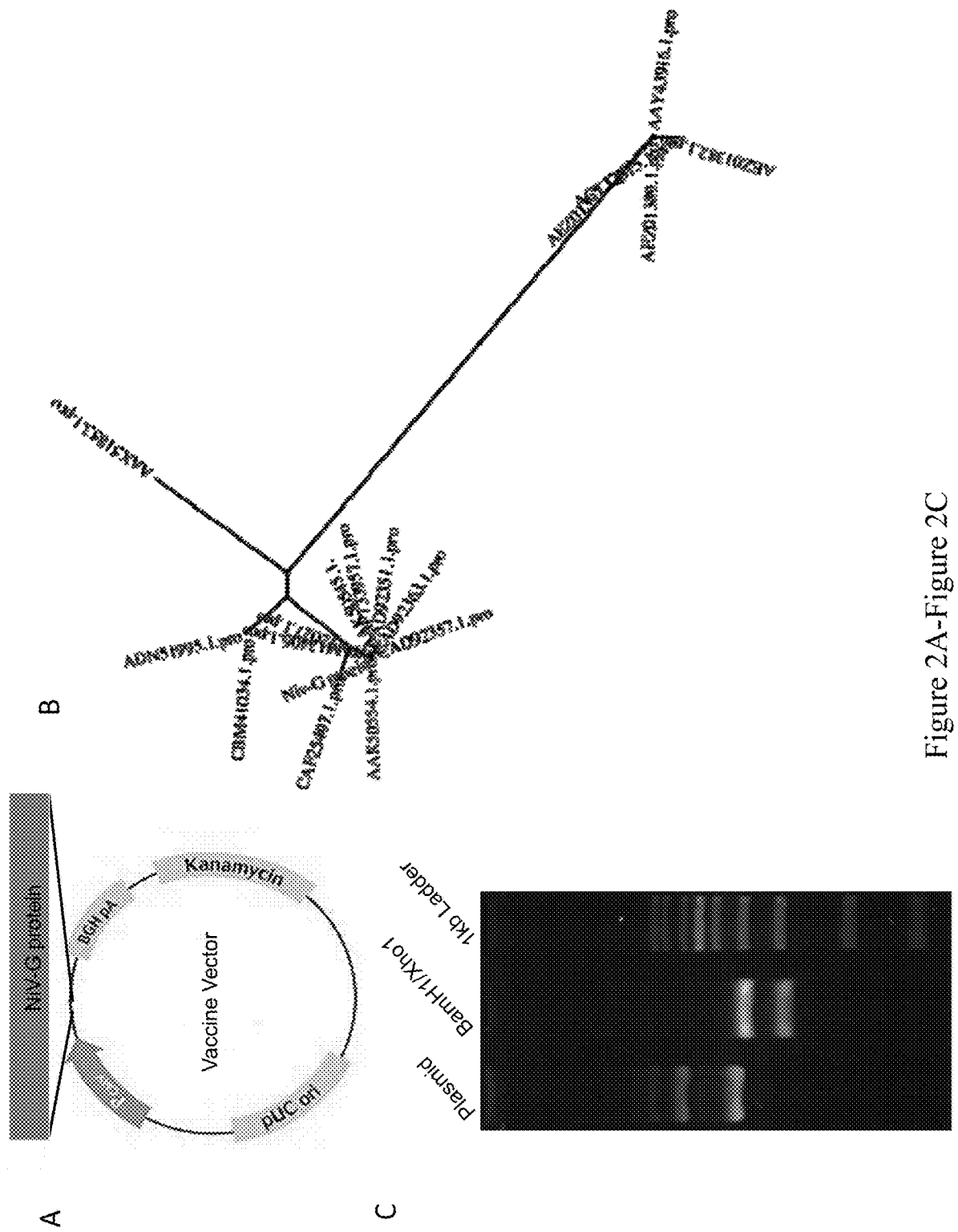
FIG. 2A through FIG. 2C, depicts the design for constructs expressing NiV-glycoprotein(G) immunogens.
Figure 3B:
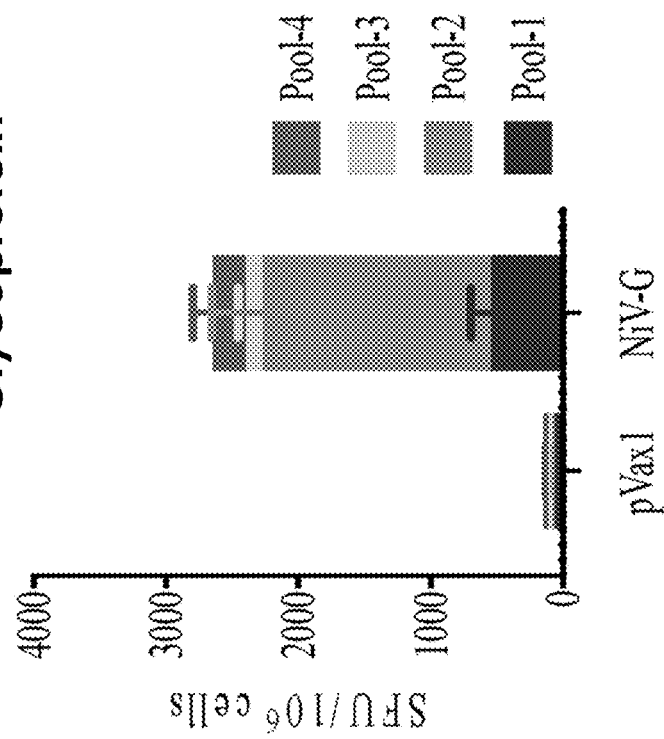
FIG. 3A through FIG. 3B, depicts the results of an exemplary NiV-F IFN-γ ELISpot assay showing a robust T cell response in NiV-F (FIG. 3A) and in NiV-G (FIG. 3B) vaccinated animals. The T cell response was reactive to all the peptide pools.
Figure 3A:
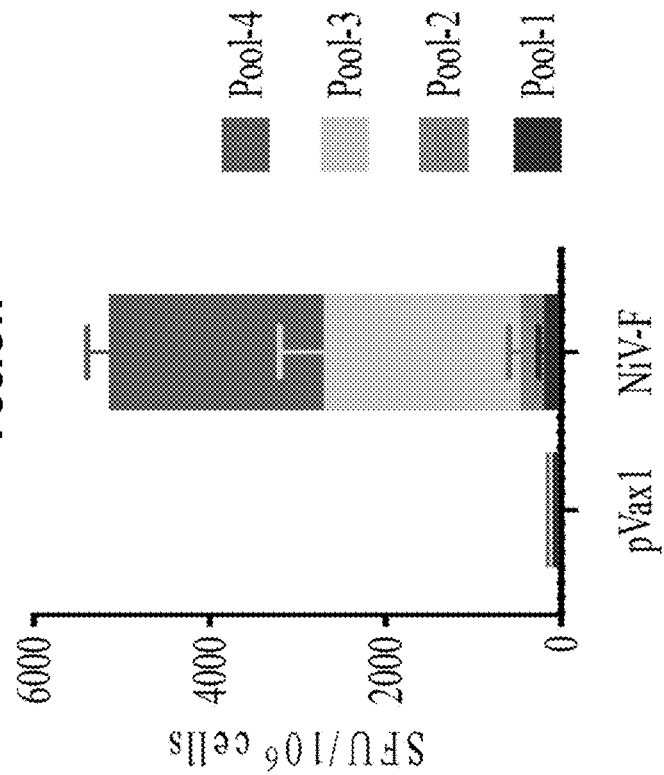
Figures 4A, 4B:
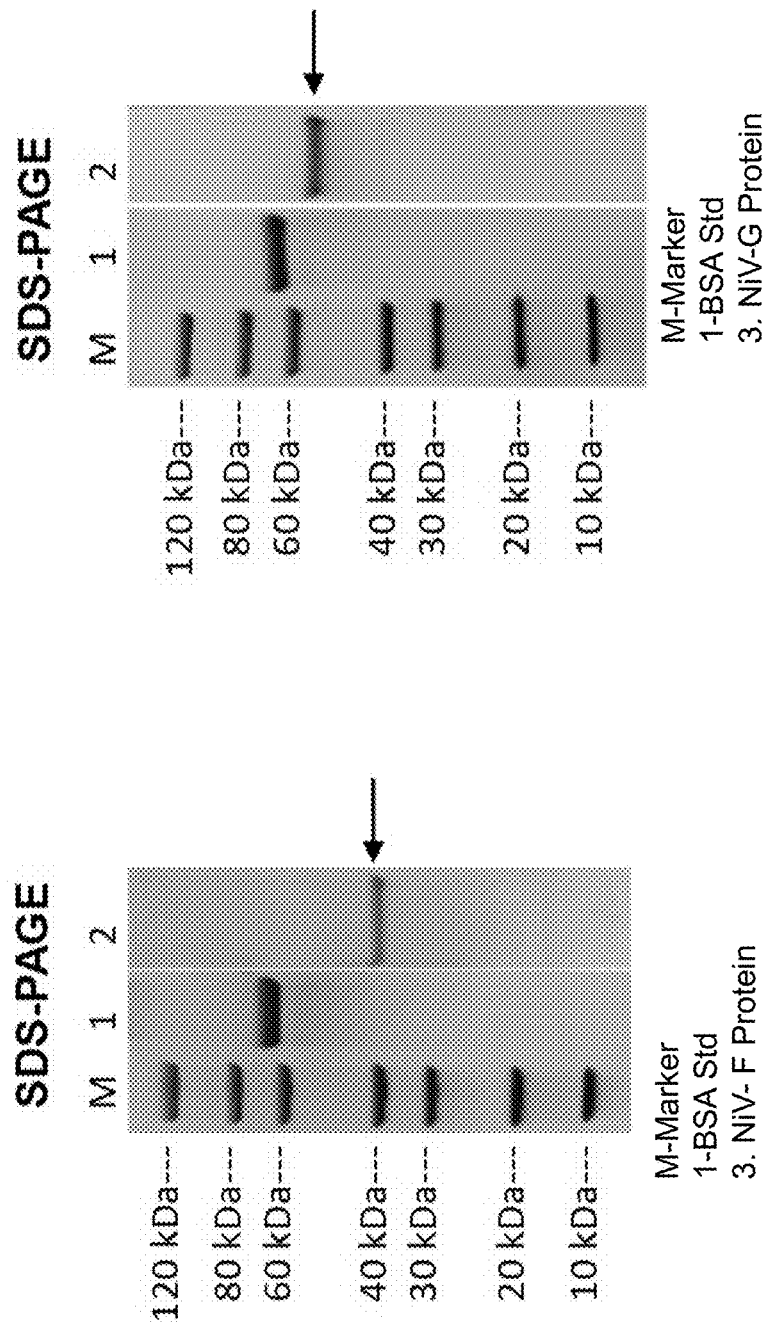
FIG. 4A through FIG. 4B, depicts exemplary experimental results demonstrating the expression, purification and characterization of NiV-F and NiV-G protein.
Figure 5B:
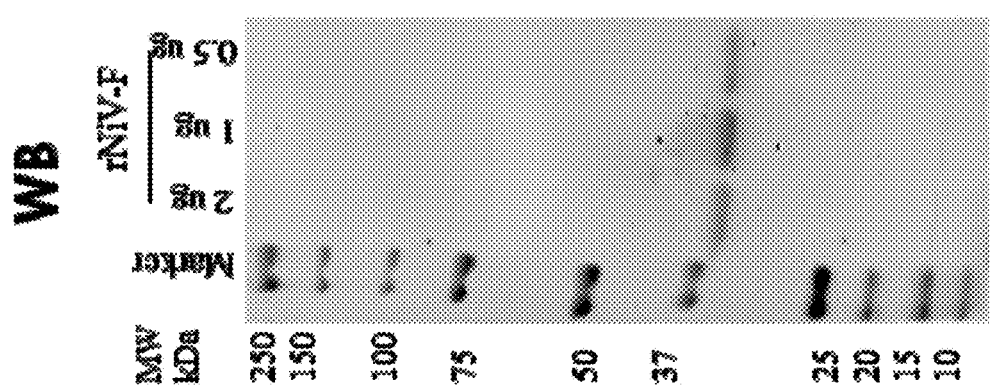
FIG. 5A through FIG. 5B, depicts exemplary data demonstrating the NiV vaccine induced humoral immune response.
Figure 5A:
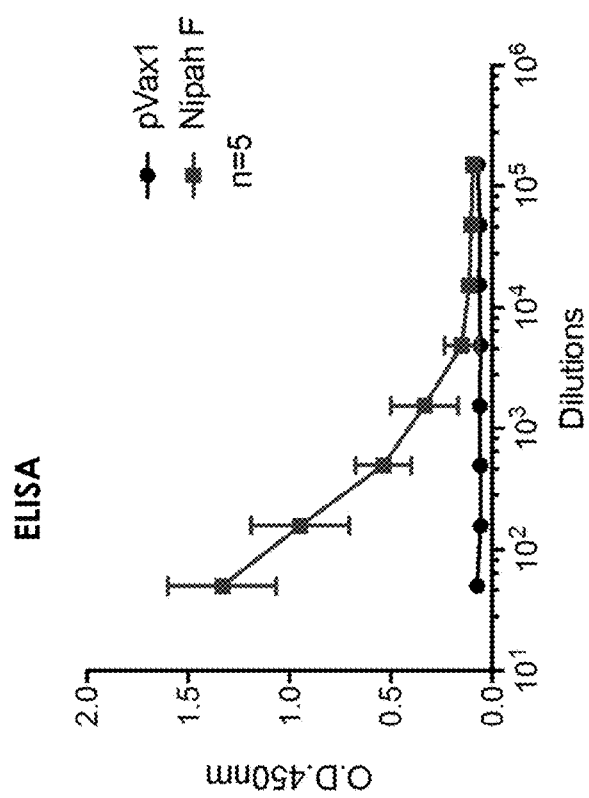
Figure 6A:
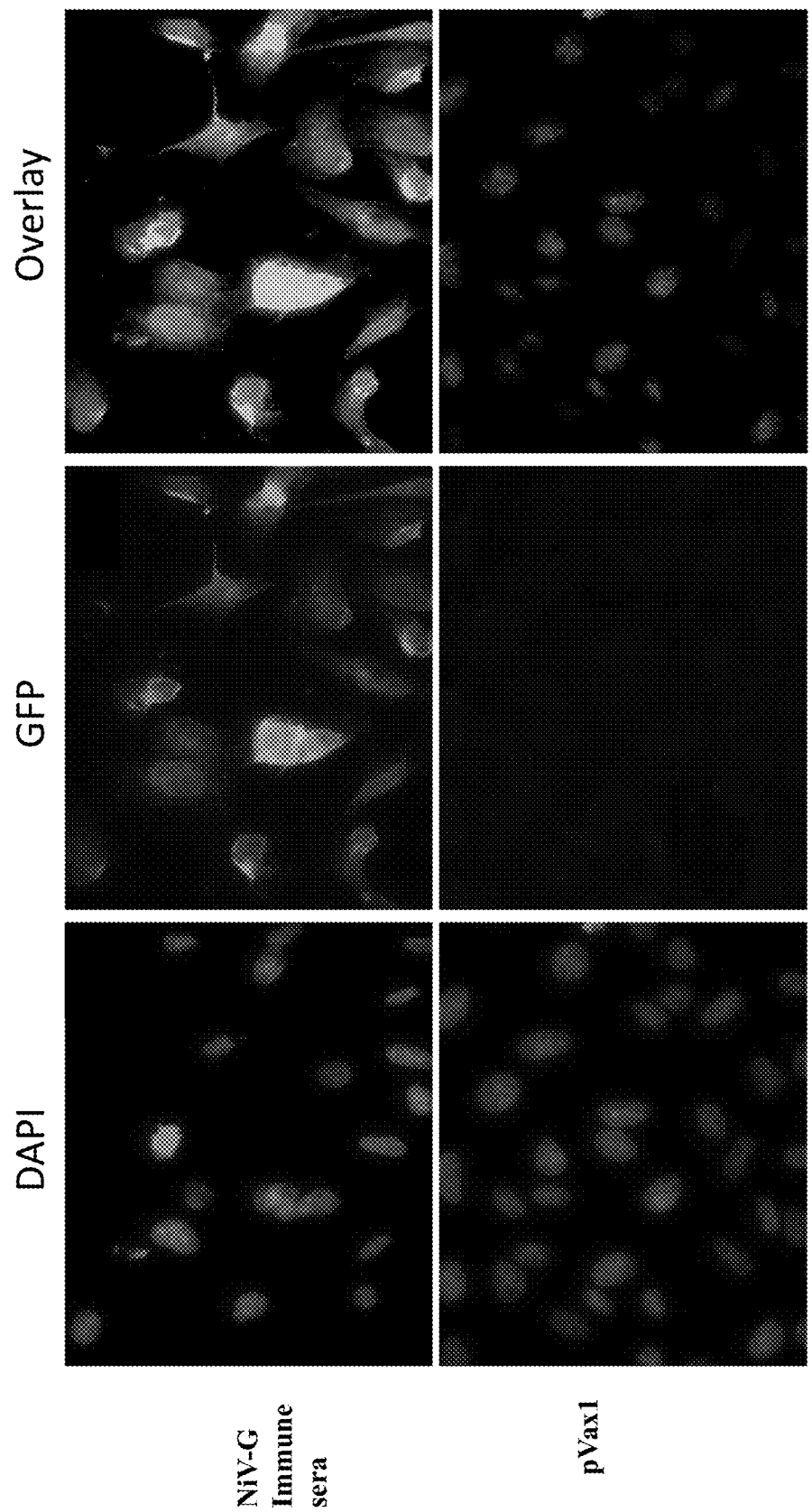
FIG. 6A and FIG. 6B, is a set of images demonstrating that NiV-G vaccine elicits an immune response.
Figure 6B:
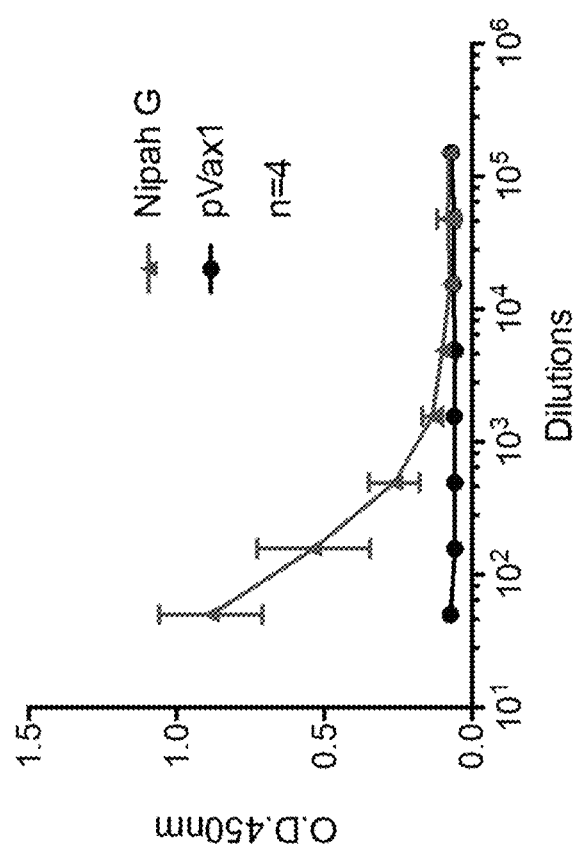
Figures 7A, 7B, 7C, 7D:
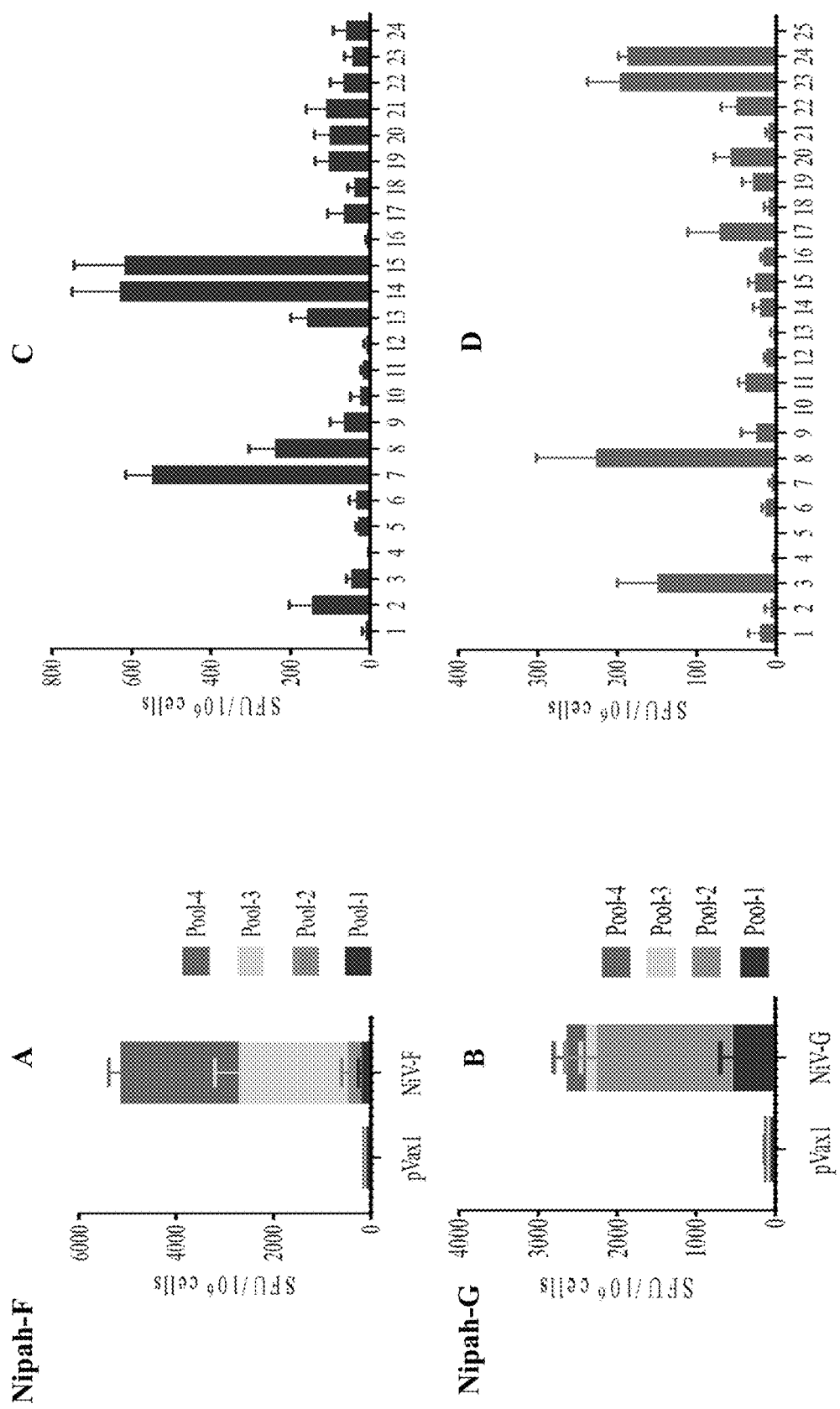
FIG. 7A through FIG. 7E, is a set of images demonstrating that nipah vaccine induces antigen-specific cellular immune responses. Nipah-specific $CD8^+$ T-lymphocyte responses were assessed by IFN-g ELISpot assays to a peptide pools of covering Nipah-Fusion (7A) and Glycoprotein (7B). Mean responses in each groups one week after the second immunization. Error bars indicate standard errors.
Figure 7E:
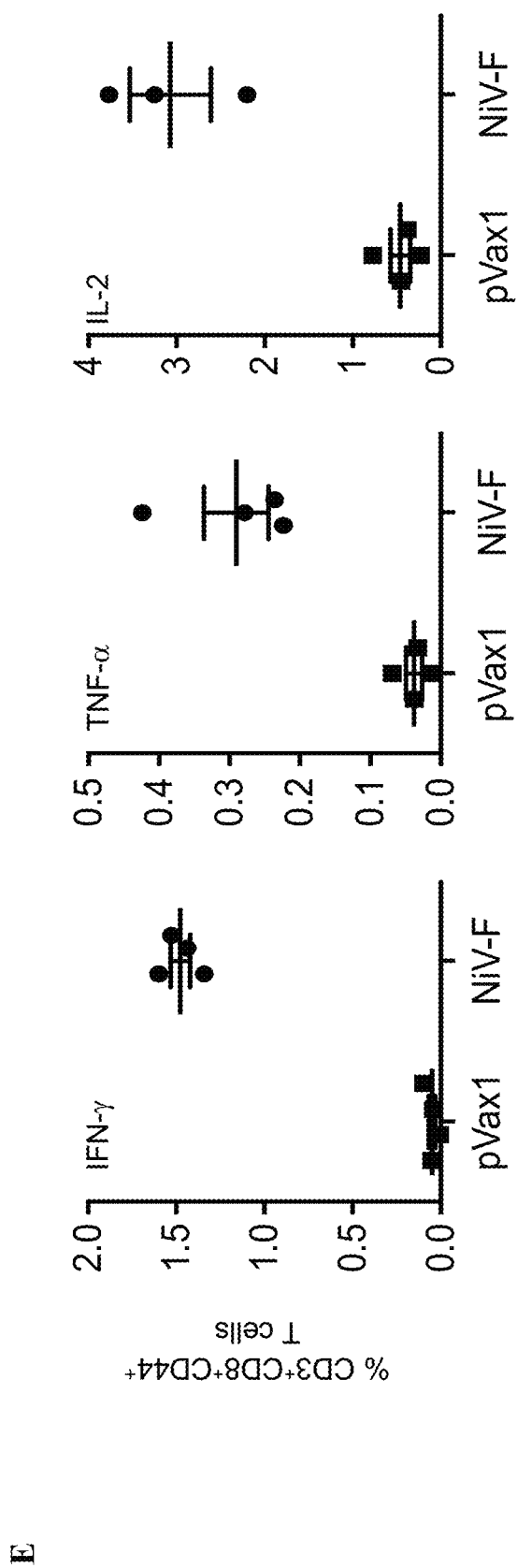

The materials and methods used are now described
Plasmid Vaccine Constructions
Plasmids were developed to express consensus NiV fusion (F) or NiV glycoprotein (G) antigens (FIG. 1 and FIG. 2).
Animals and Vaccinations
Balb/C mice were immunized with NiV-F, NiV-G or pVax1, with electroporation (EP) 2 times every 2 weeks. Sera and Splenocytes from individual mice (n=4) were isolated 1 week after the second immunization.
The results of the experiments are now described
NiV DNA Vaccine Immunogenicity in Mice
Immunogenicity and protective efficacy of NiV DNA vaccines were evaluated in mice. Mice which received three immunizations by IM-EP delivery of 25 μg NiV. Cellular responses were measured by splenocyte IFNγ ELISpot one week after final immunization. As shown in FIG. 3, NiV vaccine induced strong IFN-γ response against NiV. Antigen binding IgG ELISAs were performed to evaluate humoral immune responses in mice. The NiV vaccine induced strong binding antibodies (FIG. 5 and FIG. 6). These data indicated that the NiV DNA vaccine is immunogenic in mice provided support for further testing in larger animal species.

Example 2: Sequences

```
Nucleotide sequence of a consensus NiV-Fusion (F) immunogen
                                                    SEQ ID NO: 1
GTGGTCATCCTGGATAAGAGATGCTACTGTAACCTGCTGATCCTGATCCTGATGA

TCAGCGAGTGCTCCGTGGGCATCCTGCACTACGAGAAGCTGTCCAAGATCGGCCT

GGTGAAGGGCGTGACCCGGAAGTATAAGATCAAGTCTAATCCCCTGACAAAGGA

CATCGTGATCAAGATGATCCCTAACGTGTCTAATATGAGCCAGTGTACCGGCAGC

GTGATGGAGAACTACAAGACCCGCCTGAATGGCATCCTGACACCCATCAAGGGC

GCCCTGGAGATCTATAAGAACAATACACACGACCTGGTGGGCGATGTGAGGCTG

GCAGGCGTGATCATGGCAGGAGTGGCAATCGGAATCGCAACCGCAGCACAGATC

ACAGCAGGAGTGGCCCTGTATGAGGCCATGAAGAACGCCGACAACATCAATAAG

CTGAAGAGCTCCATCGAGTCCACCAATGAGGCCGTGGTGAAGCTGCAGGAGACA

GCCGAGAAGACAGTGTACGTGCTGACAGCCCTGCAGGACTATATCAACACCAAT

CTGGTGCCTACAATCGATAAGATCTCTTGCAAGCAGACCGAGCTGAGCCTGGACC

TGGCCCTGAGCAAGTACCTGTCCGATCTGCTGTTCGTGTTTGGCCCAAACCTGCA

GGACCCCGTGAGCAATTCCATGACAATCCAGGCCATCAGCCAGGCCTTCGGCGG

CAACTACGAGACACTGCTGAGAACACTGGGCTATGCCACCGAGGACTTTGACGA

TCTGCTGGAGTCTGATAGCATCACAGGCCAGATCATCTATGTGGACCTGTCTAGC

TACTATATCATCGTGCGGGTGTACTTCCCAATCCTGACCGAGATCCAGCAGGCCT

ATATCCAGGAGCTGCTGCCCGTGAGCTTCAACAATGATAACTCTGAGTGGATCAG

CATCGTGCCTAACTTCATCCTGGTGAGGAACACCCTGATCTCTAATATCGAGATC

GGCTTTTGCCTGATCACAAAGAGAAGCGTGATCTGTAACCAGGACTACGCCACCC

CTATGACAAACAATATGCGGGAGTGCCTGACCGGCTCCACAGAGAAGTGTCCTC

GGGAGCTGGTGGTGTCCTCTCACGTGCCACGCTTCGCCCTGTCCAACGGCGTGCT

GTTTGCCAATTGCATCTCTGTGACCTGCCAGTGTCAGACCACAGGCAGGGCCATC

TCCCAGTCTGGCGAGCAGACCCTGCTGATGATCGATAACACCACATGTCCAACA

GCCGTGCTGGGCAATGTGATCATCTCCCTGGGCAAGTACCTGGGCAGCGTGAACT
```

-continued

```
ATAATTCCGAGGGAATCGCAATCGGCCCTCCCGTGTTCACCGACAAGGTGGATAT

CAGCTCCCAGATCTCTAGCATGAACCAGTCCCTGCAGCAGTCTAAGGACTACATC

AAGGAGGCCCAGCGCCTGCTGGATACCGTGAATCCATCCCTGATCTCTATGCTGA

GCATGATCATCCTGTATGTGCTGTCCATCGCCTCTCTGTGCATCGGCCTGATCACC

TTCATCAGCTTTATCATCGTGGAGAAGAAGCGGAACACATACTCCCGCCTGGAGG

ACAGGAGAGTGAGGCCCACCTCCTCTGGCGATCTGTACTATATCGGCACA
```

SEQ ID NO: 2
amino acid sequence of a consensus NiV-Fusion (F) immunogen

```
VVILDKRCYCNLLILILMISECSVGILHYEKLSKIGLVKGVTRKYKIKSNPLTKDIVIKM

IPNVSNMSQCTGSVMENYKTRLNGILTPIKGALEIYKNNTHDLVGDVRLAGVIMAGV

AIGIATAAQITAGVALYEAMKNADNINKLKSSIESTNEAVVKLQETAEKTVYVLTAL

QDYINTNLVPTIDKISCKQTELSLDLALSKYLSDLLFVFGPNLQDPVSNSMTIQAISQA

FGGNYETLLRTLGYATEDFDDLLESDSITGQIIYVDLSSYYIIVRVYFPILTEIQQAYIQE

LLPVSFNNDNSEWISIVPNFILVRNTLISNIEIGFCLITKRSVICNQDYATPMTNNMREC

LTGSTEKCPRELVVSSHVPRFALSNGVLFANCISVTCQCQTTGRAISQSGEQTLLMID

NTTCPTAVLGNVIISLGKYLGSVNYNSEGIAIGPPVFTDKVDISSQISSMNQSLQQSKD

YIKEAQRLLDTVNPSLISMLSMIILYVLSIASLCIGLITFISFIIVEKKRNTYSRLEDRRVR

PTSSGDLYYIGT
```

SEQ ID NO: 3
Nucleotide sequence of a consensus NiV-Fusion immunogen operably linked to a sequence encoding an IgE leader and two stop codons

```
ATGGACTGGACCTGGATTCTGTTCCTGGTGGCAGCAGCAACAAGGGTGCACTCTG

TGGTCATCCTGGATAAGAGATGCTACTGTAACCTGCTGATCCTGATCCTGATGAT

CAGCGAGTGCTCCGTGGGCATCCTGCACTACGAGAAGCTGTCCAAGATCGGCCT

GGTGAAGGGCGTGACCCGGAAGTATAAGATCAAGTCTAATCCCCTGACAAAGGA

CATCGTGATCAAGATGATCCCTAACGTGTCTAATATGAGCCAGTGTACCGGCAGC

GTGATGGAGAACTACAAGACCCGCCTGAATGGCATCCTGACACCCATCAAGGGC

GCCCTGGAGATCTATAAGAACAATACACACGACCTGGTGGGCGATGTGAGGCTG

GCAGGCGTGATCATGGCAGGAGTGGCAATCGGAATCGCAACCGCAGCACAGATC

ACAGCAGGAGTGGCCCTGTATGAGGCCATGAAGAACGCCGACAACATCAATAAG

CTGAAGAGCTCCATCGAGTCCACCAATGAGGCCGTGGTGAAGCTGCAGGAGACA

GCCGAGAAGACAGTGTACGTGCTGACAGCCCTGCAGGACTATATCAACACCAAT

CTGGTGCCTACAATCGATAAGATCTCTTGCAAGCAGACCGAGCTGAGCCTGGACC

TGGCCCTGAGCAAGTACCTGTCCGATCTGCTGTTCGTGTTTGGCCCAAACCTGCA

GGACCCCGTGAGCAATTCCATGACAATCCAGGCCATCAGCCAGGCCTTCGGCGG

CAACTACGAGACACTGCTGAGAACACTGGGCTATGCCACCGAGGACTTTGACGA

TCTGCTGGAGTCTGATAGCATCACAGGCCAGATCATCTATGTGGACCTGTCTAGC

TACTATATCATCGTGCGGGTGTACTTCCCAATCCTGACCGAGATCCAGCAGGCCT

ATATCCAGGAGCTGCTGCCCGTGAGCTTCAACAATGATAACTCTGAGTGGATCAG

CATCGTGCCTAACTTCATCCTGGTGAGGAACACCCTGATCTCTAATATCGAGATC

GGCTTTTGCCTGATCACAAAGAGAAGCGTGATCTGTAACCAGGACTACGCCACCC

CTATGACAAACAATATGCGGGAGTGCCTGACCGGCTCCACAGAGAAGTGTCCTC

GGGAGCTGGTGGTGTCCTCTCACGTGCCACGCTTCGCCCTGTCCAACGGCGTGCT
```

-continued
```
GTTTGCCAATTGCATCTCTGTGACCTGCCAGTGTCAGACCACAGGCAGGGCCATC

TCCCAGTCTGGCGAGCAGACCCTGCTGATGATCGATAACACCACATGTCCAACA

GCCGTGCTGGGCAATGTGATCATCTCCCTGGGCAAGTACCTGGGCAGCGTGAACT

ATAATTCCGAGGGAATCGCAATCGGCCCTCCCGTGTTCACCGACAAGGTGGATAT

CAGCTCCCAGATCTCTAGCATGAACCAGTCCCTGCAGCAGTCTAAGGACTACATC

AAGGAGGCCCAGCGCCTGCTGGATACCGTGAATCCATCCCTGATCTCTATGCTGA

GCATGATCATCCTGTATGTGCTGTCCATCGCCTCTCTGTGCATCGGCCTGATCACC

TTCATCAGCTTTATCATCGTGGAGAAGAAGCGGAACACATACTCCCGCCTGGAGG

ACAGGAGAGTGAGGCCCACCTCCTCTGGCGATCTGTACTATATCGGCACATGATA

A
``` amino acid sequence of a consensus NiV-Fusion immunogen operably linked to an IgE leader sequence
SEQ ID NO: 4
```
MDWTWILFLVAAATRVHSVVILDKRCYCNLLILILMISECSVGILHYEKLSKIGLVKG

VTRKYKIKSNPLTKDIVIKMIPNVSNMSQCTGSVMENYKTRLNGILTPIKGALEIYKN

NTHDLVGDVRLAGVIMAGVAIGIATAAQITAGVALYEAMKNADNINKLKSSIESTNE

AVVKLQETAEKTVYVLTALQDYINTNLVPTIDKISCKQTELSLDLALSKYLSDLLFVF

GPNLQDPVSNSMTIQAISQAFGGNYETLLRTLGYATEDFDDLLESDSITGQIIYVDLSS

YYIIVRVYFPILTEIQQAYIQELLPVSFNNDNSEWISIVPNFILVRNTLISNIEIGFCLITKR

SVICNQDY ATPMTNNMRECLTGSTEKCPRELVVSSHVPRFALSNGVLFANCISVTCQ

CQTTGRAISQSGEQTLLMIDNTTCPTAVLGNVIISLGKYLGSVNYNSEGIAIGPPVFTD

KVDISSQISSMNQSLQQSKDYIKEAQRLLDTVNPSLISMLSMIILYVLSIASLCIGLITFI

SFIIVEKKRNTYSRLEDRRVRPTSSGDLYYIGT
```

Nucleotide sequence of a consensus NiV-Glycoprotein (G) immunogen
SEQ ID NO: 5
```
CCAGCCGAGAATAAGAAGGTGAGGTTTGAGAACACCACATCTGACAAGGGCAAG

ATCCCCTCTAAAGTGATCAAGAGCTACTATGGCACCATGGACATCAAGAAGATC

AATGAGGGCCTGCTGGATAGCAAGATCCTGTCCGCCTTCAACACAGTGATCGCCC

TGCTGGGCTCCATCGTGATCATCGTGATGAATATCATGATCATCCAGAACTACAC

CAGGTCTACAGACAATCAGGCCGTGATCAAGGACGCTCTGCAGGGCATCCAGCA

GCAGATCAAGGGCCTGGCCGATAAGATCGGCACAGAGATCGGCCCCAAGGTGAG

CCTGATCGACACCAGCTCCACCATCACAATCCCTGCCAACATCGGCCTGCTGGGC

AGCAAGATCTCTCAGAGCACCGCCTCCATCAACGAGAATGTGAACGAGAAGTGC

AAGTTCACACTGCCCCCTCTGAAGATCCACGAGTGCAATATCTCCTGTCCTAACC

CACTGCCCTTTAGGGAGTACAGACCACAGACCGAGGGCGTGTCTAATCTGGTGG

GCCTGCCCAACAATATCTGTCTGCAGAAGACCAGCAACCAGATCCTGAAGCCCA

AGCTGATCTCCTATACACTGCCTGTGGTGGGCCAGTCTGGCACCTGCATCACAGA

CCCTCTGCTGGCCATGGATGAGGGCTACTTCGCCTATTCTCACCTGGAGCGGATC

GGCTCCTGTTCTCGCGGCGTGAGCAAGCAGAGGATCATCGGAGTGGGAGAGGTG

CTGGACAGAGGCGATGAGGTGCCTAGCCTGTTCATGACCAACGTGTGGACACCA

CCCAATCCAAACACCGTGTACCACTGCTCCGCCGTGTATAACAATGAGTTTTACT

ACGTGCTGTGCGCCGTGAGCACCGTGGGCGATCCTATCCTGAACTCCACATACTG

GAGCGGCTCCCTGATGATGACCAGGCTGGCAGTGAAGCCAAAGAGCAATGGCGG
```

-continued
```
CGGATATAACCAGCACCAGCTGGCCCTGAGATCCATCGAGAAGGGCCGGTACGA

TAAAGTGATGCCTTATGGCCCATCCGGCATCAAGCAGGGCGACACACTGTACTTC

CCCGCCGTGGGCTTTCTGGTGAGGACCGAGTTCAAGTACAATGACTCTAACTGCC

CTATCACAAAGTGTCAGTATTCTAAGCCAGAGAATTGCCGCCTGAGCATGGGCAT

CAGGCCCAACTCTCACTACATCCTGCGCAGCGGCCTGCTGAAGTATAATCTGAGC

GACGGCGAGAACCCTAAGGTGGTGTTTATCGAGATCTCCGATCAGAGGCTGTCTA

TCGGCTCTCCCAGCAAGATCTACGACTCCCTGGGCCAGCCCGTGTTCTACCAGGC

CTCCTTTTCTTGGGACACAATGATCAAGTTCGGCGATGTGCTGACCGTGAATCCA

CTGGTGGTGAACTGGAGAAACAATACCGTGATCAGCCGGCCCGGACAGTCCCAG

TGTCCTAGGTTCAACACATGCCCAGAGATCTGTTGGGAGGGCGTGTACAATGACG

CCTTCCTGATCGATCGGATCAACTGGATCTCCGCCGGCGTGTTTCTGGACTCTAAT

CAGACCGCCGAGAACCCCGTGTTCACAGTGTTTAAGGATAATGAGATCCTGTACA

GAGCCCAGCTGGCCTCTGAGGACACCAACGCCCAGAAGACCATCACAAATTGCT

TCCTGCTGAAGAACAAGATCTGGTGTATCAGCCTGGTGGAGATCTATGACACCGG

CGATAACGTGATCCGGCCAAAGCTGTTTGCCGTGAAGATCCCCGAGCAGTGCAC

A
``` amino acid sequence of a consensus NiV-G immunogen
SEQ ID NO: 6
```
PAENKKVRFENTTSDKGKIPSKVIKSYYGTMDIKKINEGLLDSKILSAFNTVIALLGSI

VIIVMNIMIIQNYTRSTDNQAVIKDALQGIQQQIKGLADKIGTEIGPKVSLIDTSSTITIP

ANIGLLGSKISQSTASINENVNEKCKFTLPPLKIHECNISCPNPLPFREYRPQTEGVSNL

VGLPNNICLQKTSNQILKPKLISYTLPVVGQSGTCITDPLLAMDEGYFAYSHLERIGSC

SRGVSKQRIIGVGEVLDRGDEVPSLFMTNVWTPPNPNTVYHCSAVYNNEFYYVLCA

VSTVGDPILNSTYWSGSLMMTRLAVKPKSNGGGYNQHQLALRSIEKGRYDKVMPY

GPSGIKQGDTLYFPAVGFLVRTEFKYNDSNCPITKCQYSKPENCRLSMGIRPNSHYIL

RSGLLKYNLSDGENPKVVFIEISDQRLSIGSPSKIYDSLGQPVFYQASFSWDTMIKFGD

VLTVNPLVVNWRNNTVISRPGQSQCPRFNTCPEICWEGVYNDAFLIDRINWISAGVFL

DSNQTAENPVFTVFKDNEILYRAQLASEDTNAQKTITNCFLLKNKIWCISLVEIYDTG

DNVIRPKLFAVKIPEQCT
```

Nucleotide sequence of a consensus NiV-G immunogen oper-
ably linked
to a sequence encoding an IgE leader and two stop codons
SEQ ID NO: 7
```
ATGGATTGGACATGGATTCTGTTCCTGGTGGCAGCAGCAACCCGCGTGCACTCCC

CAGCCGAGAATAAGAAGGTGAGGTTTGAGAACACCACATCTGACAAGGGCAAG

ATCCCCTCTAAAGTGATCAAGAGCTACTATGGCACCATGGACATCAAGAAGATC

AATGAGGGCCTGCTGGATAGCAAGATCCTGTCCGCCTTCAACACAGTGATCGCCC

TGCTGGGCTCCATCGTGATCATCGTGATGAATATCATGATCATCCAGAACTACAC

CAGGTCTACAGACAATCAGGCCGTGATCAAGGACGCTCTGCAGGGCATCCAGCA

GCAGATCAAGGGCCTGGCCGATAAGATCGGCACAGAGATCGGCCCCAAGGTGAG

CCTGATCGACACCAGCTCCACCATCACAATCCCTGCCAACATCGGCCTGCTGGGC

AGCAAGATCTCTCAGAGCACCGCCTCCATCAACGAGAATGTGAACGAGAAGTGC

AAGTTCACACTGCCCCCTCTGAAGATCCACGAGTGCAATATCTCCTGTCCTAACC

CACTGCCCTTTAGGGAGTACAGACCACAGACCGAGGGCGTGTCTAATCTGGTGG
```

```
GCCTGCCCAACAATATCTGTCTGCAGAAGACCAGCAACCAGATCCTGAAGCCCA

AGCTGATCTCCTATACACTGCCTGTGGTGGGCCAGTCTGGCACCTGCATCACAGA

CCCTCTGCTGGCCATGGATGAGGGCTACTTCGCCTATTCTCACCTGGAGCGGATC

GGCTCCTGTTCTCGCGGCGTGAGCAAGCAGAGGATCATCGGAGTGGGAGAGGTG

CTGGACAGAGGCGATGAGGTGCCTAGCCTGTTCATGACCAACGTGTGGACACCA

CCCAATCCAAACACCGTGTACCACTGCTCCGCCGTGTATAACAATGAGTTTTACT

ACGTGCTGTGCGCCGTGAGCACCGTGGGCGATCCTATCCTGAACTCCACATACTG

GAGCGGCTCCCTGATGATGACCAGGCTGGCAGTGAAGCCAAAGAGCAATGGCGG

CGGATATAACCAGCACCAGCTGGCCCTGAGATCCATCGAGAAGGGCCGGTACGA

TAAAGTGATGCCTTATGGCCCATCCGGCATCAAGCAGGGCGACACACTGTACTTC

CCCGCCGTGGGCTTTCTGGTGAGGACCGAGTTCAAGTACAATGACTCTAACTGCC

CTATCACAAAGTGTCAGTATTCTAAGCCAGAGAATTGCCGCCTGAGCATGGGCAT

CAGGCCCAACTCTCACTACATCCTGCGCAGCGGCCTGCTGAAGTATAATCTGAGC

GACGGCGAGAACCCTAAGGTGGTGTTTATCGAGATCTCCGATCAGAGGCTGTCTA

TCGGCTCTCCCAGCAAGATCTACGACTCCCTGGGCCAGCCCGTGTTCTACCAGGC

CTCCTTTTCTTGGGACACAATGATCAAGTTCGGCGATGTGCTGACCGTGAATCCA

CTGGTGGTGAACTGGAGAAACAATACCGTGATCAGCCGGCCCGGACAGTCCCAG

TGTCCTAGGTTCAACACATGCCCAGAGATCTGTTGGGAGGGCGTGTACAATGACG

CCTTCCTGATCGATCGGATCAACTGGATCTCCGCCGGCGTGTTTCTGGACTCTAAT

CAGACCGCCGAGAACCCCGTGTTCACAGTGTTTAAGGATAATGAGATCCTGTACA

GAGCCCAGCTGGCCTCTGAGGACACCAACGCCCAGAAGACCATCACAAATTGCT

TCCTGCTGAAGAACAAGATCTGGTGTATCAGCCTGGTGGAGATCTATGACACCGG

CGATAACGTGATCCGGCCAAAGCTGTTTGCCGTGAAGATCCCCGAGCAGTGCAC

ATGATAA
``` amino acid sequence of a consensus NiV-G immunogen operably
linked to an IgE leader sequence

SEQ ID NO: 8

```
MDWTWILFLVAAATRVHSPAENKKVRFENTTSDKGKIPSKVIKSYYGTMDIKKINEG

LLDSKILSAFNTVIALLGSIVIIVMNIMIIQNYTRSTDNQAVIKDALQGIQQQIKGLADK

IGTEIGPKVSLIDTSSTITIPANIGLLGSKISQSTASINENVNEKCKFTLPPLKIHECNISCP

NPLPFREYRPQTEGVSNLVGLPNNICLQKTSNQILKPKLISYTLPVVGQSGTCITDPLL

AMDEGYFAYSHLERIGSCSRGVSKQRIIGVGEVLDRGDEVPSLFMTNVWTPPNPNTV

YHCSAVYNNEFYYVLCAVSTVGDPILNSTYWSGSLMMTRLAVKPKSNGGGYNQHQ

LALRSIEKGRYDKVMPYGPSGIKQGDTLYFPAVGFLVRTEFKYNDSNCPITKCQYSK

PENCRLSMGIRPNSHYILRSGLLKYNLSDGENPKVVFIEISDQRLSIGSPSKIYDSLGQP

VFYQASFSWDTMIKFGDVLTVNPLVVNWRNNTVISRPGQSQCPRFNTCPEICWEGV

YNDAFLIDRINWISAGVFLDSNQTAENPVFTVFKDNEILYRAQLASEDTNAQKTITNC

FLLKNKIWCISLVEIYDTGDNVIRPKLFAVKIPEQCT
```

IgE leader

SEQ ID NO: 9

```
MDWTWILFLVAAATRVHS
```

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A nucleic acid molecule encoding at least one consensus Nipah virus (NiV) antigen, wherein the nucleic acid molecule comprises a sequence selected from the group consisting of
   a) a nucleotide sequence having at least 98% identity over an entire length of the nucleotide sequence selected from the group consisting of SEQ ID NO:1 and SEQ ID NO:5,
   b) an immunogenic fragment comprising at least 98% identity over at least 60% of the nucleotide sequence selected from the group consisting of SEQ ID NO:1 and SEQ ID NO:5, and
   c) the nucleotide sequence selected from the group consisting of SEQ ID NO:1 and SEQ ID NO:5.

2. The nucleic acid molecule of claim 1, wherein the nucleic acid molecule is selected from the group consisting of a DNA molecule and an RNA molecule.

3. The nucleic acid molecule of claim 1, wherein the nucleotide sequence further comprises at least one operably linked regulatory sequence selected from the group consisting of a start codon, a nucleotide sequence encoding an IgE leader sequence and a stop codon.

4. The nucleic acid molecule of claim 3, wherein the nucleic acid molecule is operably linked to a nucleotide sequence encoding SEQ ID NO:9.

5. The nucleic acid molecule of claim 1, wherein the nucleic acid molecule comprises an expression vector.

6. The nucleic acid molecule of claim 1, wherein the nucleic acid molecule comprises a viral particle.

7. An immunogenic composition comprising a nucleic acid molecule of claim 1.

8. The immunogenic composition of claim 7, further comprising at least one selected from the group consisting of a pharmaceutically acceptable excipient and an adjuvant.

9. A method of inducing an immune response against a NiV antigen in a subject in need thereof, the method comprising administering an immunogenic composition of claim 7 to the subject.

10. The method of claim 9, wherein administering includes at least one of electroporation and injection.

11. A method of treating or preventing a NiV associated pathology in subject in need thereof, the method comprising administering an immunogenic composition of claim 7 to the subject.

12. The method of claim 11, wherein administering includes at least one of electroporation and injection.

13. The method of claim 11, wherein the NiV associated pathology is at least one of NiV infection and encephalitis.

* * * * *

SEQUENCE LISTING

```
<160> NUMBER OF SEQ ID NOS: 9

<210> SEQ ID NO 1
<211> LENGTH: 1635
<212> TYPE: DNA
<213> ORGANISM: Artificial Sequence
<220> FEATURE:
<223> OTHER INFORMATION: Nucleotide sequence of a consensus NiV-Fusion
      (F) immunogen

<400> SEQUENCE: 1
gtggtcatcc tggataagag atgctactgt aacctgctga tcctgatcct gatgatcagc        60
gagtgctccg tgggcatcct gcactacgag aagctgtcca agatcggcct ggtgaagggc       120
gtgacccgga agtataagat caagtctaat cccctgacaa aggacatcgt gatcaagatg       180
atccctaacg tgtctaatat gagccagtgt accggcagcg tgatggagaa ctacaagacc       240
cgcctgaatg catcctgac acccatcaag ggcgccctgg agatctataa gaacaataca       300
cacgacctgg tgggcgatgt gaggctggca ggcgtgatca tggcaggagt ggcaatcgga       360
atcgcaaccg cagcacagat cacagcagga gtggccctgt atgaggccat gaagaacgcc       420
gacaacatca ataagctgaa gagctccatc gagtccacca tgaggccgt ggtgaagctg       480 caggagacag ccgagaagac agtgtacgtg ctgacagccc tgcaggacta tatcaacacc       540
aatctggtgc ctacaatcga taagatctct tgcaagcaga ccgagctgag cctggacctg       600
gccctgagca agtacctgtc cgatctgctg ttcgtgtttg cccaaacct gcaggacccc       660 gtgagcaatt ccatgacaat ccaggccatc agccaggcct tcggcggcaa ctacgagaca       720
ctgctgagaa cactgggcta tgccaccgag gactttgacg atctgctgga gtctgatagc       780
atcacaggcc agatcatcta tgtggacctg tctagctact atatcatcgt gcgggtgtac       840
ttcccaatcc tgaccgagat ccagcaggcc tatatccagg agctgctgcc cgtgagcttc       900
aacaatgata actctgagtg gatcagcatc gtgcctaact tcatcctggt gaggaacacc       960
ctgatctcta atatcgagat cggcttttgc ctgatcacaa agagaagcgt gatctgtaac      1020
caggactacg ccaccccctat gacaaacaat atgcgggagt gcctgaccgg ctccacagag      1080
aagtgtcctc gggagctggt ggtgtcctct cacgtgccac gcttcgccct gtccaacggc      1140
gtgctgtttg ccaattgcat ctctgtgacc tgccagtgtc agaccacagg cagggccatc      1200
tcccagtctg gcgagcagac cctgctgatg atcgataaca ccacatgtcc aacagccgtg      1260
ctgggcaatg tgatcatctc cctgggcaag tacctgggca gcgtgaacta taattccgag      1320
ggaatcgcaa tcggccctcc cgtgttcacc gacaaggtgg atatcagctc ccagatctct      1380
agcatgaacc agtccctgca gcagtctaag gactacatca aggaggccca gcgcctgctg      1440
gataccgtga atccatccct gatctctatg ctgagcatga tcatcctgta tgtgctgtcc      1500
atcgcctctc tgtgcatcgg cctgatcacc ttcatcagct ttatcatcgt ggagaagaag      1560
cggaacacat actcccgcct ggaggacagg agagtgaggc ccacctcctc tggcgatctg      1620
tactatatcg gcaca                                                        1635
```

<210> SEQ ID NO 2
<211> LENGTH: 545
<212> TYPE: PRT
<213> ORGANISM: Artificial Sequence
<220> FEATURE:
<223> OTHER INFORMATION: Amino acid sequence of a consensus NiV-Fusion (F) immunogen

<400> SEQUENCE: 2

```
Val Val Ile Leu Asp Lys Arg Cys Tyr Cys Asn Leu Leu Ile Leu Ile
1               5                   10                  15

Leu Met Ile Ser Glu Cys Ser Val Gly Ile Leu His Tyr Glu Lys Leu
            20                  25                  30

Ser Lys Ile Gly Leu Val Lys Gly Val Thr Arg Lys Tyr Lys Ile Lys
        35                  40                  45

Ser Asn Pro Leu Thr Lys Asp Ile Val Ile Lys Met Ile Pro Asn Val
    50                  55                  60

Ser Asn Met Ser Gln Cys Thr Gly Ser Val Met Glu Asn Tyr Lys Thr
65                  70                  75                  80

Arg Leu Asn Gly Ile Leu Thr Pro Ile Lys Gly Ala Leu Glu Ile Tyr
                85                  90                  95

Lys Asn Asn Thr His Asp Leu Val Gly Asp Val Arg Leu Ala Gly Val
            100                 105                 110

Ile Met Ala Gly Val Ala Ile Gly Ile Ala Thr Ala Ala Gln Ile Thr
        115                 120                 125

Ala Gly Val Ala Leu Tyr Glu Ala Met Lys Asn Ala Asp Asn Ile Asn
    130                 135                 140

Lys Leu Lys Ser Ser Ile Glu Ser Thr Asn Glu Ala Val Val Lys Leu
145                 150                 155                 160

Gln Glu Thr Ala Glu Lys Thr Val Tyr Val Leu Thr Ala Leu Gln Asp
                165                 170                 175

Tyr Ile Asn Thr Asn Leu Val Pro Thr Ile Asp Lys Ile Ser Cys Lys
            180                 185                 190

Gln Thr Glu Leu Ser Leu Asp Leu Ala Leu Ser Lys Tyr Leu Ser Asp
        195                 200                 205

Leu Leu Phe Val Phe Gly Pro Asn Leu Gln Asp Pro Val Ser Asn Ser
    210                 215                 220

Met Thr Ile Gln Ala Ile Ser Gln Ala Phe Gly Gly Asn Tyr Glu Thr
225                 230                 235                 240

Leu Leu Arg Thr Leu Gly Tyr Ala Thr Glu Asp Phe Asp Asp Leu Leu
                245                 250                 255

Glu Ser Asp Ser Ile Thr Gly Gln Ile Ile Tyr Val Asp Leu Ser Ser
            260                 265                 270

Tyr Tyr Ile Ile Val Arg Val Tyr Phe Pro Ile Leu Thr Glu Ile Gln
        275                 280                 285

Gln Ala Tyr Ile Gln Glu Leu Leu Pro Val Ser Phe Asn Asn Asp Asn
    290                 295                 300

Ser Glu Trp Ile Ser Ile Val Pro Asn Phe Ile Leu Val Arg Asn Thr
305                 310                 315                 320

Leu Ile Ser Asn Ile Glu Ile Gly Phe Cys Leu Ile Thr Lys Arg Ser
                325                 330                 335

Val Ile Cys Asn Gln Asp Tyr Ala Thr Pro Met Thr Asn Asn Met Arg
            340                 345                 350

Glu Cys Leu Thr Gly Ser Thr Glu Lys Cys Pro Arg Glu Leu Val Val
        355                 360                 365
```

```
Ser Ser His Val Pro Arg Phe Ala Leu Ser Asn Gly Val Leu Phe Ala
    370             375                 380

Asn Cys Ile Ser Val Thr Cys Gln Cys Gln Thr Thr Gly Arg Ala Ile
385             390                 395                 400

Ser Gln Ser Gly Glu Gln Thr Leu Leu Met Ile Asp Asn Thr Thr Cys
            405                 410                 415

Pro Thr Ala Val Leu Gly Asn Val Ile Ile Ser Leu Gly Lys Tyr Leu
            420                 425                 430

Gly Ser Val Asn Tyr Asn Ser Glu Gly Ile Ala Ile Gly Pro Pro Val
            435                 440                 445

Phe Thr Asp Lys Val Asp Ile Ser Ser Gln Ile Ser Ser Met Asn Gln
    450                 455                 460

Ser Leu Gln Gln Ser Lys Asp Tyr Ile Lys Glu Ala Gln Arg Leu Leu
465             470                 475                 480

Asp Thr Val Asn Pro Ser Leu Ile Ser Met Leu Ser Met Ile Ile Leu
            485                 490                 495

Tyr Val Leu Ser Ile Ala Ser Leu Cys Ile Gly Leu Ile Thr Phe Ile
            500                 505                 510

Ser Phe Ile Ile Val Glu Lys Lys Arg Asn Thr Tyr Ser Arg Leu Glu
    515                 520                 525

Asp Arg Arg Val Arg Pro Thr Ser Ser Gly Asp Leu Tyr Tyr Ile Gly
    530                 535                 540

Thr
545

<210> SEQ ID NO 3
<211> LENGTH: 1695
<212> TYPE: DNA
<213> ORGANISM: Artificial Sequence
<220> FEATURE:
<223> OTHER INFORMATION: Nucleotide sequence of a consensus NiV-Fusion
      immunogen operably linked to a sequence encoding an IgE leader and
      two stop codons

<400> SEQUENCE: 3
atggactgga cctggattct gttcctggtg gcagcagcaa caagggtgca ctctgtggtc      60
atcctggata gagatgcta ctgtaacctg ctgatcctga tcctgatgat cagcgagtgc     120
tccgtgggca tcctgcacta cgagaagctg tccaagatcg gctggtgaa gggcgtgacc     180 cggaagtata gatcaagtc taatcccctg acaaggaca tcgtgatcaa gatgatccct     240
aacgtgtcta tatgagcca gtgtaccggc agcgtgatgg agaactacaa gacccgcctg     300
aatggcatcc tgacacccat caagggcgcc ctggagatct ataagaacaa tacacacgac     360
ctggtgggcg atgtgaggct ggcaggcgtg atcatggcag gagtggcaat cggaatcgca     420
accgcagcac agatcacagc aggagtggcc ctgtatgagg ccatgaagaa cgccgacaac     480
atcaataagc tgaagagctc catcgagtcc accaatgagg ccgtggtgaa gctgcaggag     540
acagccgaga agacagtgta cgtgctgaca gccctgcagg actatatcaa caccaatctg     600
gtgcctacaa tcgataagat ctcttgcaag cagaccgagc tgagcctgga cctggccctg     660
agcaagtacc tgtccgatct gctgttcgtg tttggcccaa acctgcagga ccccgtgagc     720
aattccatga caatccaggc catcagccag gccttcggcg gcaactacga gacactgctg     780
agaacactgg gctatgccac cgaggacttt gacgatctgc tggagtctga tagcatcaca     840
ggccagatca tctatgtgga cctgtctagc tactatatca tcgtgcgggt gtacttccca     900
```

```
atcctgaccg agatccagca ggcctatatc caggagctgc tgcccgtgag cttcaacaat    960
gataactctg agtggatcag catcgtgcct aacttcatcc tggtgaggaa caccctgatc   1020
tctaatatcg agatcggctt tgcctgatca caaagagaa gcgtgatctg taaccaggac   1080
tacgccaccc ctatgacaaa caatatgcgg gagtgcctga ccggctccac agagaagtgt   1140
cctcgggagc tggtggtgtc ctctcacgtg ccacgcttcg ccctgtccaa cggcgtgctg   1200
tttgccaatt gcatctctgt gacctgccag tgtcagacca caggcagggc catctcccag   1260
tctggcgagc agaccctgct gatgatcgat aacaccacat gtccaacagc cgtgctgggc   1320
aatgtgatca tctccctggg caagtacctg ggcagcgtga actataattc cgagggaatc   1380
gcaatcggcc ctcccgtgtt caccgacaag gtggatatca gctcccagat ctctagcatg   1440
aaccagtccc tgcagcagtc taaggactac atcaaggagg cccagcgcct gctggatacc   1500
gtgaatccat ccctgatctc tatgctgagc atgatcatcc tgtatgtgct gtccatcgcc   1560
tctctgtgca tcggcctgat caccttcatc agctttatca tcgtggagaa gaagcggaac   1620
acatactccc gcctggagga caggagagtg aggcccacct cctctggcga tctgtactat   1680
atcggcacat gataa                                                    1695
```

<210> SEQ ID NO 4
<211> LENGTH: 563
<212> TYPE: PRT
<213> ORGANISM: Artificial Sequence
<220> FEATURE:
<223> OTHER INFORMATION: Amino acid sequence of a consensus NiV-Fusion immunogen operably linked to an IgE leader sequence

<400> SEQUENCE: 4

```
Met Asp Trp Thr Trp Ile Leu Phe Leu Val Ala Ala Thr Arg Val
1               5                   10                  15

His Ser Val Val Ile Leu Asp Lys Arg Cys Tyr Cys Asn Leu Leu Ile
            20                  25                  30

Leu Ile Leu Met Ile Ser Glu Cys Ser Val Gly Ile Leu His Tyr Glu
        35                  40                  45

Lys Leu Ser Lys Ile Gly Leu Val Lys Gly Val Thr Arg Lys Tyr Lys
    50                  55                  60

Ile Lys Ser Asn Pro Leu Thr Lys Asp Ile Val Ile Lys Met Ile Pro
65                  70                  75                  80

Asn Val Ser Asn Met Ser Gln Cys Thr Gly Ser Val Met Glu Asn Tyr
                85                  90                  95

Lys Thr Arg Leu Asn Gly Ile Leu Thr Pro Ile Lys Gly Ala Leu Glu
            100                 105                 110

Ile Tyr Lys Asn Asn Thr His Asp Leu Val Gly Asp Val Arg Leu Ala
        115                 120                 125

Gly Val Ile Met Ala Gly Val Ala Ile Gly Ile Ala Thr Ala Ala Gln
    130                 135                 140

Ile Thr Ala Gly Val Ala Leu Tyr Glu Ala Met Lys Asn Ala Asp Asn
145                 150                 155                 160

Ile Asn Lys Leu Lys Ser Ser Ile Glu Ser Thr Asn Glu Ala Val Val
                165                 170                 175

Lys Leu Gln Glu Thr Ala Glu Lys Thr Val Tyr Val Leu Thr Ala Leu
            180                 185                 190

Gln Asp Tyr Ile Asn Thr Asn Leu Val Pro Thr Ile Asp Lys Ile Ser
        195                 200                 205

Cys Lys Gln Thr Glu Leu Ser Leu Asp Leu Ala Leu Ser Lys Tyr Leu
```

```
                  210                 215                 220
Ser Asp Leu Leu Phe Val Phe Gly Pro Asn Leu Gln Asp Pro Val Ser
225                 230                 235                 240

Asn Ser Met Thr Ile Gln Ala Ile Ser Gln Ala Phe Gly Gly Asn Tyr
                245                 250                 255

Glu Thr Leu Leu Arg Thr Leu Gly Tyr Ala Thr Glu Asp Phe Asp Asp
                260                 265                 270

Leu Leu Glu Ser Asp Ser Ile Thr Gly Gln Ile Ile Tyr Val Asp Leu
                275                 280                 285

Ser Ser Tyr Tyr Ile Ile Val Arg Val Tyr Phe Pro Ile Leu Thr Glu
290                 295                 300

Ile Gln Gln Ala Tyr Ile Gln Glu Leu Leu Pro Val Ser Phe Asn Asn
305                 310                 315                 320

Asp Asn Ser Glu Trp Ile Ser Ile Val Pro Asn Phe Ile Leu Val Arg
                325                 330                 335

Asn Thr Leu Ile Ser Asn Ile Glu Ile Gly Phe Cys Leu Ile Thr Lys
                340                 345                 350

Arg Ser Val Ile Cys Asn Gln Asp Tyr Ala Thr Pro Met Thr Asn Asn
                355                 360                 365

Met Arg Glu Cys Leu Thr Gly Ser Thr Glu Lys Cys Pro Arg Glu Leu
370                 375                 380

Val Val Ser Ser His Val Pro Arg Phe Ala Leu Ser Asn Gly Val Leu
385                 390                 395                 400

Phe Ala Asn Cys Ile Ser Val Thr Cys Gln Cys Gln Thr Thr Gly Arg
                405                 410                 415

Ala Ile Ser Gln Ser Gly Glu Gln Thr Leu Leu Met Ile Asp Asn Thr
                420                 425                 430

Thr Cys Pro Thr Ala Val Leu Gly Asn Val Ile Ile Ser Leu Gly Lys
                435                 440                 445

Tyr Leu Gly Ser Val Asn Tyr Asn Ser Glu Gly Ile Ala Ile Gly Pro
                450                 455                 460

Pro Val Phe Thr Asp Lys Val Asp Ile Ser Ser Gln Ile Ser Ser Met
465                 470                 475                 480

Asn Gln Ser Leu Gln Gln Ser Lys Asp Tyr Ile Lys Glu Ala Gln Arg
                485                 490                 495

Leu Leu Asp Thr Val Asn Pro Ser Leu Ile Ser Met Leu Ser Met Ile
                500                 505                 510

Ile Leu Tyr Val Leu Ser Ile Ala Ser Leu Cys Ile Gly Leu Ile Thr
                515                 520                 525

Phe Ile Ser Phe Ile Ile Val Glu Lys Lys Arg Asn Thr Tyr Ser Arg
                530                 535                 540

Leu Glu Asp Arg Arg Val Arg Pro Thr Ser Ser Gly Asp Leu Tyr Tyr
545                 550                 555                 560

Ile Gly Thr
```

<210> SEQ ID NO 5
<211> LENGTH: 1803
<212> TYPE: DNA
<213> ORGANISM: Artificial Sequence
<220> FEATURE:
<223> OTHER INFORMATION: Nucleotide sequence of a consensus
      NiV-Glycoprotein (G) immunogen

<400> SEQUENCE: 5
ccagccgaga ataagaaggt gaggtttgag aacaccacat ctgacaaggg caagatcccc     60

-continued

```
tctaaagtga tcaagagcta ctatggcacc atggacatca agaagatcaa tgagggcctg      120
ctggatagca agatcctgtc cgccttcaac acagtgatcg ccctgctggg ctccatcgtg      180
atcatcgtga tgaatatcat gatcatccag aactacacca ggtctacaga caatcaggcc      240
gtgatcaagg acgctctgca gggcatccag cagcagatca agggcctggc cgataagatc      300
ggcacagaga tcggccccaa ggtgagcctg atcgacacca gctccaccat cacaatccct      360
gccaacatcg gcctgctggg cagcaagatc tctcagagca ccgcctccat caacgagaat      420
gtgaacgaga agtgcaagtt cacactgccc cctctgaaga tccacgagtg caatatctcc      480
tgtcctaacc cactgccctt tagggagtac agaccacaga ccgagggcgt gtctaatctg      540
gtgggcctgc ccaacaatat ctgtctgcag aagaccagca ccagatcct gaagcccaag      600 ctgatctcct atacactgcc tgtggtgggc cagtctggca cctgcatcac agaccctctg      660
ctggccatgg atgagggcta cttcgcctat tctcacctgg agcggatcgg ctcctgttct      720
cgcggcgtga gcaagcagag gatcatcgga gtgggagagg tgctggacag aggcgatgag      780
gtgcctagcc tgttcatgac caacgtgtgg acaccaccca atccaaacac cgtgtaccac      840
tgctccgccg tgtataacaa tgagttttac tacgtgctgt cgccgtgag caccgtgggc      900 gatcctatcc tgaactccac atactggagc ggctccctga tgatgaccag gctggcagtg      960
aagccaaaga gcaatggcgg cggatataac cagcaccagc tggccctgag atccatcgag     1020
aagggccggt acgataaagt gatgcccta ggcccatccg gcatcaagca gggcgacaca     1080
ctgtacttcc ccgccgtggg ctttctggtg aggaccgagt tcaagtacaa tgactctaac     1140
tgccctatca caaagtgtca gtattctaag ccagagaatt gccgcctgag catgggcatc     1200
aggcccaact ctcactacat cctgcgcagc ggcctgctga agtataatct gagcgacggc     1260 gagaaccta aggtggtgtt tatcgagatc tccgatcaga ggctgtctat cggctctccc     1320
agcaagatct acgactccct gggccagccc gtgttctacc aggcctccctt ttcttgggac     1380 acaatgatca agttcggcga tgtgctgacc gtgaatccac tggtggtgaa ctggagaaac     1440
aataccgtga tcagccggcc cggacagtcc cagtgtccta ggttcaacac atgcccagag     1500
atctgttggg agggcgtgta caatgacgcc ttcctgatcg atcggatcaa ctggatctcc     1560
gccggcgtgt tctctggactc taatcagacc gccgagaacc ccgtgttcac agtgtttaag     1620
gataatgaga tcctgtacag agcccagctg gcctctgagg acaccaacgc ccagaagacc     1680
atcacaaatt gcttcctgct gaagaacaag atctggtgta tcagcctggt ggagatctat     1740
gacaccggcg ataacgtgat ccggccaaag ctgtttgccg tgaagatccc cgagcagtgc     1800
aca                                                                    1803
```

<210> SEQ ID NO 6
<211> LENGTH: 601
<212> TYPE: PRT
<213> ORGANISM: Artificial Sequence
<220> FEATURE:
<223> OTHER INFORMATION: Amino acid sequence of a consensus NiV-G
      immunogen

<400> SEQUENCE: 6

Pro Ala Glu Asn Lys Lys Val Arg Phe Glu Asn Thr Thr Ser Asp Lys
1               5                   10                  15

Gly Lys Ile Pro Ser Lys Val Ile Lys Ser Tyr Tyr Gly Thr Met Asp
            20                  25                  30

Ile Lys Lys Ile Asn Glu Gly Leu Leu Asp Ser Lys Ile Leu Ser Ala

```
                35                  40                  45
Phe Asn Thr Val Ile Ala Leu Leu Gly Ser Ile Val Ile Val Met
 50                  55                  60

Asn Ile Met Ile Ile Gln Asn Tyr Thr Arg Ser Thr Asp Asn Gln Ala
 65                  70                  75                  80

Val Ile Lys Asp Ala Leu Gln Gly Ile Gln Gln Ile Lys Gly Leu
                 85                  90                  95

Ala Asp Lys Ile Gly Thr Glu Ile Gly Pro Lys Val Ser Leu Ile Asp
                100                 105                 110

Thr Ser Ser Thr Ile Thr Ile Pro Ala Asn Ile Gly Leu Leu Gly Ser
                115                 120                 125

Lys Ile Ser Gln Ser Thr Ala Ser Ile Asn Glu Asn Val Asn Glu Lys
130                 135                 140

Cys Lys Phe Thr Leu Pro Pro Leu Lys Ile His Glu Cys Asn Ile Ser
145                 150                 155                 160

Cys Pro Asn Pro Leu Pro Phe Arg Glu Tyr Arg Pro Gln Thr Glu Gly
                165                 170                 175

Val Ser Asn Leu Val Gly Leu Pro Asn Asn Ile Cys Leu Gln Lys Thr
                180                 185                 190

Ser Asn Gln Ile Leu Lys Pro Lys Leu Ile Ser Tyr Thr Leu Pro Val
                195                 200                 205

Val Gly Gln Ser Gly Thr Cys Ile Thr Asp Pro Leu Leu Ala Met Asp
210                 215                 220

Glu Gly Tyr Phe Ala Tyr Ser His Leu Glu Arg Ile Gly Ser Cys Ser
225                 230                 235                 240

Arg Gly Val Ser Lys Gln Arg Ile Ile Gly Val Gly Glu Val Leu Asp
                245                 250                 255

Arg Gly Asp Glu Val Pro Ser Leu Phe Met Thr Asn Val Trp Thr Pro
                260                 265                 270

Pro Asn Pro Asn Thr Val Tyr His Cys Ser Ala Val Tyr Asn Asn Glu
                275                 280                 285

Phe Tyr Tyr Val Leu Cys Ala Val Ser Thr Val Gly Asp Pro Ile Leu
290                 295                 300

Asn Ser Thr Tyr Trp Ser Gly Ser Leu Met Met Thr Arg Leu Ala Val
305                 310                 315                 320

Lys Pro Lys Ser Asn Gly Gly Tyr Asn Gln His Gln Leu Ala Leu
                325                 330                 335

Arg Ser Ile Glu Lys Gly Arg Tyr Asp Lys Val Met Pro Tyr Gly Pro
                340                 345                 350

Ser Gly Ile Lys Gln Gly Asp Thr Leu Tyr Phe Pro Ala Val Gly Phe
                355                 360                 365

Leu Val Arg Thr Glu Phe Lys Tyr Asn Asp Ser Asn Cys Pro Ile Thr
                370                 375                 380

Lys Cys Gln Tyr Ser Lys Pro Glu Asn Cys Arg Leu Ser Met Gly Ile
385                 390                 395                 400

Arg Pro Asn Ser His Tyr Ile Leu Arg Ser Gly Leu Leu Lys Tyr Asn
                405                 410                 415

Leu Ser Asp Gly Glu Asn Pro Lys Val Val Phe Ile Glu Ile Ser Asp
                420                 425                 430

Gln Arg Leu Ser Ile Gly Ser Pro Lys Ile Tyr Asp Ser Leu Gly
                435                 440                 445

Gln Pro Val Phe Tyr Gln Ala Ser Phe Ser Trp Asp Thr Met Ile Lys
450                 455                 460
```

Phe Gly Asp Val Leu Thr Val Asn Pro Leu Val Asn Trp Arg Asn
465                 470                 475                 480

Asn Thr Val Ile Ser Arg Pro Gly Gln Ser Gln Cys Pro Arg Phe Asn
            485                 490                 495

Thr Cys Pro Glu Ile Cys Trp Glu Gly Val Tyr Asn Asp Ala Phe Leu
        500                 505                 510

Ile Asp Arg Ile Asn Trp Ile Ser Ala Gly Val Phe Leu Asp Ser Asn
            515                 520                 525

Gln Thr Ala Glu Asn Pro Val Phe Thr Val Phe Lys Asp Asn Glu Ile
        530                 535                 540

Leu Tyr Arg Ala Gln Leu Ala Ser Glu Asp Thr Asn Ala Gln Lys Thr
545                 550                 555                 560

Ile Thr Asn Cys Phe Leu Leu Lys Asn Lys Ile Trp Cys Ile Ser Leu
            565                 570                 575

Val Glu Ile Tyr Asp Thr Gly Asp Asn Val Ile Arg Pro Lys Leu Phe
        580                 585                 590

Ala Val Lys Ile Pro Glu Gln Cys Thr
        595                 600

<210> SEQ ID NO 7
<211> LENGTH: 1863
<212> TYPE: DNA
<213> ORGANISM: Artificial Sequence
<220> FEATURE:
<223> OTHER INFORMATION: Nucleotide sequence of a consensus NiV-G
      immunogen operably linked to a sequence encoding an IgE leader and
      two stop codons

<400> SEQUENCE: 7
atggattgga catgattct gttcctggtg gcagcagcaa cccgcgtgca ctccccagcc      60
gagaataaga aggtgaggtt tgagaacacc acatctgaca agggcaagat cccctctaaa    120
gtgatcaaga gctactatgg caccatggac atcaagaaga tcaatgaggg cctgctggat    180
agcaagatcc tgtccgcctt caacacagtg atcgccctgc tgggctccat cgtgatcatc    240
gtgatgaata tcatgatcat ccagaactac accaggtcta cagacaatca ggccgtgatc    300
aaggacgctc tgcagggcat ccagcagcag atcaagggcc tggccgataa gatcggcaca    360
gagatcggcc ccaaggtgag cctgatcgac accagctcca ccatcacaat ccctgccaac    420
atcggcctgc tgggcagcaa gatctctcag agcaccgcct ccatcaacga gaatgtgaac    480
gagaagtgca gttcacact gcccctctg aagatccacg agtgcaatat ctcctgtcct    540
aacccactgc cctttaggga gtacagacca cagaccgagg gcgtgtctaa tctggtgggc    600
ctgcccaaca atatctgtct gcagaagacc agcaaccaga tcctgaagcc aagctgatc    660 tcctatacac tgcctgtggt gggccagtct ggcacctgca tcacagaccc tctgctggcc    720
atggatgagg ctacttcgc ctattctcac ctggagcgga tcggctcctg ttctcgcggc    780
gtgagcaagc agaggatcat cggagtggga gaggtgctgg acagaggcga tgaggtgcct    840
agcctgttca tgaccaacgt gtggacacca cccaatccaa acaccgtgta ccactgctcc    900
gccgtgtata caatgagtt ttactacgtg ctgtgcgccg tgagcaccgt gggcgatcct    960
atcctgaact ccacatactg gagcggctcc ctgatgatga ccaggctggc agtgaagcca   1020
aagagcaatg cggcggata taaccagcac cagctggccc tgagatccat cgagaagggc   1080
cggtacgata aagtgatgcc ttatggccca tccggcatca gcagggcga cacactgtac   1140 ttccccgccg tgggctttct ggtgaggacc gagttcaagt acaatgactc taactgccct   1200

```
atcacaaagt gtcagtattc taagccagag aattgccgcc tgagcatggg catcaggccc    1260
aactctcact acatcctgcg cagcggcctg ctgaagtata atctgagcga cggcgagaac    1320
cctaaggtgg tgtttatcga gatctccgat cagaggctgt ctatcggctc tcccagcaag    1380
atctacgact ccctgggcca gcccgtgttc taccaggcct ccttttcttg ggacacaatg    1440
atcaagttcg gcgatgtgct gaccgtgaat ccactggtgg tgaactggag aaacaatacc    1500
gtgatcagcc ggcccggaca gtcccagtgt cctaggttca acacatgccc agagatctgt    1560
tgggagggcg tgtacaatga cgccttcctg atcgatcgga tcaactggat ctccgccggc    1620
gtgtttctgg actctaatca gaccgccgag aaccccgtgt tcacagtgtt taaggataat    1680
gagatcctgt acagagccca gctggcctct gaggacacca cgcccagaa gaccatcaca    1740 aattgcttcc tgctgaagaa caagatctgg tgtatcagcc tggtggagat ctatgacacc    1800
ggcgataacg tgatccggcc aaagctgttt gccgtgaaga tccccgagca gtgcacatga    1860
taa                                                                  1863
```

<210> SEQ ID NO 8
<211> LENGTH: 619
<212> TYPE: PRT
<213> ORGANISM: Artificial Sequence
<220> FEATURE:
<223> OTHER INFORMATION: Amino acid sequence of a consensus NiV-G
      immunogen operably linked to an IgE leader sequence

<400> SEQUENCE: 8

Met Asp Trp Thr Trp Ile Leu Phe Leu Val Ala Ala Ala Thr Arg Val
1 5 10 15

His Ser Pro Ala Glu Asn Lys Lys Val Arg Phe Glu Asn Thr Thr Ser
20 25 30

Asp Lys Gly Lys Ile Pro Ser Lys Val Ile Lys Ser Tyr Tyr Gly Thr
35 40 45

Met Asp Ile Lys Lys Ile Asn Glu Gly Leu Leu Asp Ser Lys Ile Leu
50 55 60

Ser Ala Phe Asn Thr Val Ile Ala Leu Leu Gly Ser Ile Val Ile Ile
65 70 75 80

Val Met Asn Ile Met Ile Ile Gln Asn Tyr Thr Arg Ser Thr Asp Asn
85 90 95

Gln Ala Val Ile Lys Asp Ala Leu Gln Gly Ile Gln Gln Gln Ile Lys
100 105 110

Gly Leu Ala Asp Lys Ile Gly Thr Glu Ile Gly Pro Lys Val Ser Leu
115 120 125

Ile Asp Thr Ser Ser Thr Ile Thr Ile Pro Ala Asn Ile Gly Leu Leu
130 135 140

Gly Ser Lys Ile Ser Gln Ser Thr Ala Ser Ile Asn Glu Asn Val Asn
145 150 155 160

Glu Lys Cys Lys Phe Thr Leu Pro Pro Leu Lys Ile His Glu Cys Asn
165 170 175

Ile Ser Cys Pro Asn Pro Leu Pro Phe Arg Glu Tyr Arg Pro Gln Thr
180 185 190

Glu Gly Val Ser Asn Leu Val Gly Leu Pro Asn Asn Ile Cys Leu Gln
195 200 205

Lys Thr Ser Asn Gln Ile Leu Lys Pro Lys Leu Ile Ser Tyr Thr Leu
210 215 220

Pro Val Val Gly Gln Ser Gly Thr Cys Ile Thr Asp Pro Leu Leu Ala

```
            225                 230                 235                 240
Met Asp Glu Gly Tyr Phe Ala Tyr Ser His Leu Glu Arg Ile Gly Ser
                245                 250                 255

Cys Ser Arg Gly Val Ser Lys Gln Arg Ile Ile Gly Val Gly Glu Val
                260                 265                 270

Leu Asp Arg Gly Asp Glu Val Pro Ser Leu Phe Met Thr Asn Val Trp
                275                 280                 285

Thr Pro Pro Asn Pro Asn Thr Val Tyr His Cys Ser Ala Val Tyr Asn
290                 295                 300

Asn Glu Phe Tyr Tyr Val Leu Cys Ala Val Ser Thr Val Gly Asp Pro
305                 310                 315                 320

Ile Leu Asn Ser Thr Tyr Trp Ser Gly Ser Leu Met Met Thr Arg Leu
                325                 330                 335

Ala Val Lys Pro Lys Ser Asn Gly Gly Tyr Asn Gln His Gln Leu
                340                 345                 350

Ala Leu Arg Ser Ile Glu Lys Gly Arg Tyr Asp Lys Val Met Pro Tyr
                355                 360                 365

Gly Pro Ser Gly Ile Lys Gln Gly Asp Thr Leu Tyr Phe Pro Ala Val
                370                 375                 380

Gly Phe Leu Val Arg Thr Glu Phe Lys Tyr Asn Asp Ser Asn Cys Pro
385                 390                 395                 400

Ile Thr Lys Cys Gln Tyr Ser Lys Pro Glu Asn Cys Arg Leu Ser Met
                405                 410                 415

Gly Ile Arg Pro Asn Ser His Tyr Ile Leu Arg Ser Gly Leu Leu Lys
                420                 425                 430

Tyr Asn Leu Ser Asp Gly Glu Asn Pro Lys Val Val Phe Ile Glu Ile
                435                 440                 445

Ser Asp Gln Arg Leu Ser Ile Gly Ser Pro Ser Lys Ile Tyr Asp Ser
                450                 455                 460

Leu Gly Gln Pro Val Phe Tyr Gln Ala Ser Phe Ser Trp Asp Thr Met
465                 470                 475                 480

Ile Lys Phe Gly Asp Val Leu Thr Val Asn Pro Leu Val Val Asn Trp
                485                 490                 495

Arg Asn Asn Thr Val Ile Ser Arg Pro Gly Gln Ser Gln Cys Pro Arg
                500                 505                 510

Phe Asn Thr Cys Pro Glu Ile Cys Trp Glu Gly Val Tyr Asn Asp Ala
                515                 520                 525

Phe Leu Ile Asp Arg Ile Asn Trp Ile Ser Ala Gly Val Phe Leu Asp
                530                 535                 540

Ser Asn Gln Thr Ala Glu Asn Pro Val Phe Thr Val Phe Lys Asp Asn
545                 550                 555                 560

Glu Ile Leu Tyr Arg Ala Gln Leu Ala Ser Glu Asp Thr Asn Ala Gln
                565                 570                 575

Lys Thr Ile Thr Asn Cys Phe Leu Leu Lys Asn Lys Ile Trp Cys Ile
                580                 585                 590

Ser Leu Val Glu Ile Tyr Asp Thr Gly Asp Asn Val Ile Arg Pro Lys
                595                 600                 605

Leu Phe Ala Val Lys Ile Pro Glu Gln Cys Thr
610                 615
```

<210> SEQ ID NO 9
<211> LENGTH: 18
<212> TYPE: PRT
<213> ORGANISM: Artificial Sequence

```
<220> FEATURE:
<223> OTHER INFORMATION: IgE leader

<400> SEQUENCE: 9

Met Asp Trp Thr Trp Ile Leu Phe Leu Val Ala Ala Ala Thr Arg Val
1               5                   10                  15

His Ser
```